(12) United States Patent
Koenemann et al.

(10) Patent No.: US 9,919,999 B2
(45) Date of Patent: Mar. 20, 2018

(54) CYANATED PERYLENE COMPOUNDS

(71) Applicant: BASF SE, Ludwigshafen (DE)

(72) Inventors: Martin Koenemann, Mannheim (DE);
Gerhard Wagenblast, Wachenheim (DE); Sorin Ivanovici, Heidelberg (DE); Robert Send, Karlsruhe (DE);
Gabriele Mattern, Schifferstadt (DE);
Gerd Weber, Bad Duerkheim (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 15/309,631

(22) PCT Filed: May 8, 2015

(86) PCT No.: PCT/EP2015/060137
§ 371 (c)(1),
(2) Date: Nov. 8, 2016

(87) PCT Pub. No.: WO2015/169935
PCT Pub. Date: Nov. 12, 2015

(65) Prior Publication Data
US 2017/0183295 A1    Jun. 29, 2017

(30) Foreign Application Priority Data

May 9, 2014 (EP) .................................. 14167746

(51) Int. Cl.
*C07C 255/57* (2006.01)
*C09K 11/06* (2006.01)
*C07C 255/52* (2006.01)
*C09K 11/77* (2006.01)

(52) U.S. Cl.
CPC .......... *C07C 255/57* (2013.01); *C07C 255/52* (2013.01); *C09K 11/06* (2013.01); *C09K 11/7774* (2013.01); *C09K 2211/1011* (2013.01)

(58) Field of Classification Search
CPC ...................... C07C 255/57; C09K 2211/1011
See application file for complete search history.

(56) References Cited

U.S. PATENT DOCUMENTS

| | | |
|---|---|---|
| 7,311,858 B2 | 12/2007 | Wang et al. |
| 7,755,276 B2 | 7/2010 | Wang et al. |
| 7,906,041 B2 | 3/2011 | Li et al. |
| 8,274,215 B2 | 9/2012 | Liu et al. |
| 2004/0062699 A1 | 4/2004 | Oshio |
| 2013/0284265 A1 | 10/2013 | Jiang et al. |
| 2014/0076397 A1 | 3/2014 | Wagenblast et al. |
| 2016/0177177 A1 | 6/2016 | Koenemann et al. |

FOREIGN PATENT DOCUMENTS

| | | |
|---|---|---|
| JP | 11-273864 A | 10/1999 |
| WO | 98/28946 A1 | 7/1998 |
| WO | 2004/029028 A2 | 4/2004 |
| WO | 2007/006717 A1 | 1/2007 |
| WO | 2012/010244 A1 | 1/2012 |
| WO | 2012/094409 A2 | 7/2012 |
| WO | 2012/152812 A1 | 11/2012 |

(Continued)

OTHER PUBLICATIONS

International Search Report dated Jul. 20, 2015 in PCT/EP2015/060137 filed May 8, 2015.
U.S. Appl. No. 14/992,761, filed Jan. 11, 2016, 2014/012002, Ingmar Bruder.
U.S. Appl. No. 14/440,637, filed May 5, 2015, 2015/318501, Soichi Watanabe.
U.S. Appl. No. 14/016,514, filed Sep. 3, 2014, 2014/066656, Ingmar Bruder.
U.S. Appl. No. 15/309,631, filed Nov. 8, 2016, Martin Koenemann.
U.S. Appl. No. 14/413,736, filed Jan. 9, 2015, 2015/207083, Thomas Schaefer.

(Continued)

*Primary Examiner* — Golam M M Shameem
(74) *Attorney, Agent, or Firm* — Oblon, McClelland, Maier & Neustadt, L.L.P.

(57) ABSTRACT

The present invention relates to a cyanated perylene compound of the formula I

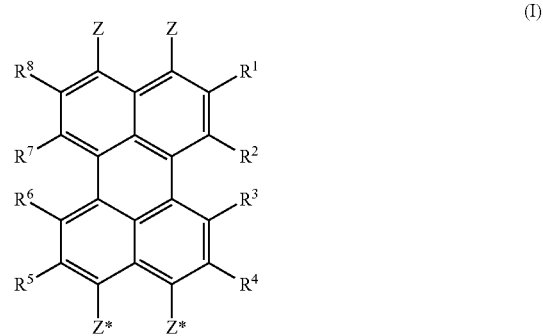

(I)

in which
one of the Z substituents and one of the Z* substituents are cyano and the other Z substituent and the other Z* substituent are each independently $CO_2R^9$, $CONR^{10}R^{11}$, optionally substituted alkyl, alkenyl, alkynyl, cycloalkyl or $C_6$-$C_{14}$-aryl, where $R^9$, $R^{10}$ and $R^{11}$ are each as defined in the claims; and mixtures thereof.
The present invention further relates to a composition comprising a cyanated perylene compound of the formula I or mixtures thereof and to a process for preparation thereof; to color converters comprising at least one polymer as matrix material and at least one cyanated perylene compound or mixtures thereof or a composition comprising at least one cyanated perylene compound or mixtures thereof as fluorescent dye; to the use of these color converters and to lighting devices comprising at least one LED and at least one color converter.

11 Claims, No Drawings

(56) References Cited

FOREIGN PATENT DOCUMENTS

| WO | 2012/168395 A1 | 12/2012 |
|---|---|---|
| WO | 2015/019270 A1 | 2/2015 |

OTHER PUBLICATIONS

U.S. Appl. No. 14/746,113, filed Jun. 22, 2015, 2015/284569, Henrike Wonneberger.
U.S. Appl. No. 14/427,134, filed Mar. 10, 2015, 2015/243907, Annemarie Wolleb.
U.S. Appl. No. 14/907,100, filed Jan. 22, 2016, 2016/155575, Hitoshi Yamato.
U.S. Appl. No. 14/132,570, filed Dec. 18, 2013, 2014/291480, Ingmar Bruder.
U.S. Appl. No. 14/758,349, filed Jun. 29, 2015, 2015/0333275, Henrike Wonneberger.
U.S. Appl. No. 14/897,981, filed Dec. 11, 2015, 2016/0124074A1, Henrike Wonneberger.
U.S. Appl. No. 14/778,400, filed Sep. 18, 2015, 2016/141521, Soichi Watanabe.
U.S. Appl. No. 14/786,507, filed Oct. 22, 2015, 2016/072081, Stefan Metz.
U.S. Appl. No. 14/896,958, filed Dec. 9, 2015, 2016/127664A1, Ingmar Bruder.
U.S. Appl. No. 14/901,738, filed Dec. 29, 2015, 2016-0372687A1, Peter Murer.
U.S. Appl. No. 14/913,817, filed Feb. 23, 2016, 2016/248021, Sudhakar Sundarraj.
U.S. Appl. No. 14/913,860, filed Feb. 23, 2016, 2016/211464, Junichi Tanabe.
U.S. Appl. No. 14/787,909, filed Oct. 29, 2015, 2016/0099429, Ingmar Bruder.
U.S. Appl. No. 14/460,540, filed Aug. 15, 2014, 2015/0286340, Robert Send.
U.S. Appl. No. 14/460,529, filed Aug. 15, 2014, 2016-0364015, Robert Send.
U.S. Appl. No. 14/910,078, filed Feb. 4, 2016, 2016-0177177, Martin Könemann.
U.S. Appl. No. 14/908,606, filed Jan. 29, 2016, 2016-0181549, Peter Murer.
U.S. Appl. No. 15/105,489, filed Jun. 16, 2016, 2016-0320489, Robert Send.
U.S. Appl. No. 15/305,379, filed Oct. 20, 2016, Robert Send.
U.S. Appl. No. 15/105,947, filed Jun. 17, 2016, 2016-0315274, Christian Lennartz.
U.S. Appl. No. 15/301,112, Robert Send.

CYANATED PERYLENE COMPOUNDS

The present invention relates to novel cyanated perylene compounds and mixtures thereof, to compositions comprising at least one cyanated perylene compound or mixtures thereof, and to processes for preparation thereof. The present invention further relates to color converters comprising at least one polymer as matrix material and at least one cyanated perylene compound or mixtures thereof or a composition comprising at least one cyanated perylene compound or mixtures thereof as fluorescent dye, to the use of these color converters and to lighting devices comprising at least one LED and at least one color converter.

Because of their low energy consumption, LEDs (light-emitting diodes, LEDs) are increasingly being used as a light source for general lighting, for example in offices and residences, or for architectural lighting, in information signs, small appliances, and in the automobile and aircraft industries. Light emission is based on the recombination of electron-hole pairs (excitons) in the junction region of a pn junction poled in forward direction in a semiconductor. The size of the band gap of this semiconductor determines the approximate wavelength of the light emitted. In order to generate a particular color, LEDs with different band gaps can be combined to form a multi-LED.

Alternatively, a radiation conversion luminophore (also referred to as phosphor, or fluorescent colorant or fluorescent dye) can also be combined with an LED. In this context, the radiation emitted by the LED is partly absorbed by the radiation conversion luminophore, which is thus induced to photoluminesce. The resulting light color of the LED results from the proportion of LED light transmitted and the emission spectrum of the radiation conversion luminophore. In one method, for this purpose, a polymeric material comprising a radiation conversion luminophore is applied directly to the LED light source (LED chip). Frequently, the polymeric material is applied to the LED chip, for instance, in droplet form or in hemispherical form, as a result of which particular optical effects contribute to the emission of the light. Setups of this kind, in which radiation conversion luminophore in a polymeric matrix is applied directly and without any intermediate space to an LED chip, are also referred to as "phosphor on a chip". In phosphor on a chip LEDs, the radiation conversion luminophores used are generally inorganic materials. In phosphor on a chip LEDs, the polymeric material and the radiation conversion luminophore are subject to relatively high thermal stress and radiation stress. For this reason, organic radiation conversion luminophores have not been suitable to date for use in phosphor on a chip LEDs.

In another method, the color converter (also referred to as "converter" or "light converter"), which generally comprises a polymer layer and a radiation conversion luminophore, is at a certain distance from the LED chip. A setup of this kind is referred to as "remote phosphor".

The spatial distance between the primary light source, the LED, and the color converter reduces the stress resulting from heat and radiation to such an extent that organic fluorescent dyes can also be used as radiation conversion luminophores. Furthermore, LEDs according to the "remote phosphor" concept are more energy-efficient than those according to the "phosphor on a chip" concept. The use of organic fluorescent dyes in these converters offers various advantages. Firstly, the hue of the light has good adjustability with fluorescent dyes. Secondly, there is no requirement for materials comprising rare earths, which have to be obtained by mining and provided in a costly and inconvenient manner and are available only to a limited extent.

White light-emitting LEDs are used in many application sectors as a lighting source or as a backlight in full-color displays. White light can be generated in various ways with LEDs. The basis for the emission of white light is always the superimposition (mixing) of various colors. In what are called multi-LEDs, for example, three light-emitting diodes which emit light in different colors, generally one blue, one green and one red, or two light-emitting diodes which emit light in complementary colors, one blue and one yellow, are combined in a housing. Because of the different brightnesses and operating conditions for the various light-emitting diodes, the multi-LED is technically complex and therefore expensive. Moreover, component miniaturization of the multi-LED is severely limited.

White light can also be generated by applying at least one radiation converter to an LED which preferably emits blue light having a wavelength of 400 to 500 nm. The radiation conversion luminophore used is frequently cerium-doped yttrium aluminum garnet (also referred to as hereinafter as Ce:YAG). Ce is a luminophore which exhibits a broad emission band having a maximum at about 560 nm. According to the concentration of the radiation converter, portions of the blue light emitted by the LED are absorbed and converted to luminescence light which is yellow for the most part, such that the mixing of the blue light transmitted and the yellow light emitted gives rise to white light. The white hue or the color temperature of the LED therefore depends on the layer thickness and the exact composition of the Ce:YAG radiation converter. LEDs based on a blue-emitting LED and Ce:YAG are easy to produce. For simple applications in which color rendering and hue are of minor importance, the LED based on the blue-emitting Ce:YAG LED is of good suitability. Since the red component in the spectrum is absent, the blue portion dominates the light emitted. Therefore, an LED based on a blue-emitting LED and YAG as a sole radiation conversion luminophore is unsuitable for many applications. For applications in which high-quality color rendering is desired, the light radiation of the LED in the wavelength range from 460 to 580 nm is inadequate. A further disadvantage is the use of materials comprising rare earths, such as Ce:YAG, as explained above.

The color rendering index (CRI) is understood to mean a photometric parameter which gives an assessment of a light source in comparison to an ideal light source (Planckian radiator) with regard to quality in terms of the color rendering of up to 14 listed reference colors (CIE 1974). The size of the CRI value may be between 0 and 100 and describes the extent to which a light source is able to render the different colors of reference colors. The first commercially available white light LEDs had color rendering of 70 to 80. Sunlight has a CRI of up to 100.

WO 2012/168395 describes color converters which comprise at least one polymer and at least one organic fluorescent dye, wherein the organic fluorescent dye comprises at least one structural unit of the formula (A)

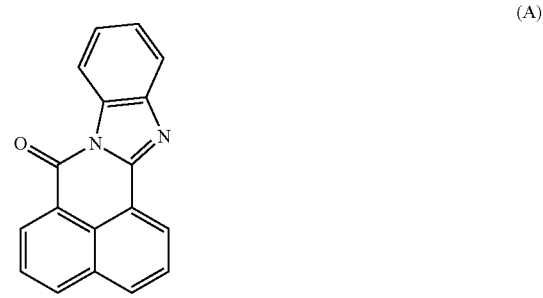

(A)

where the structural unit may be mono- or polysubstituted by identical or different substituents and where one or more CH groups in the six-membered ring of the benzimidazole structure shown may be replaced by nitrogen. Cyanated fluorescent dyes are not described in this document.

The unpublished EP 13179303.6 describes cyanated naphthalenebenzimidazole compounds and mixtures thereof, the use thereof in color converters, the use of the color converters and lighting devices comprising at least one LED and at least one color converter.

Some of the organic fluorescent dyes known from the prior art are unsatisfactory in terms of their photostability with respect to blue light in the wavelength range from 400 to 500 nm and/or the fluorescence quantum yield in polymeric matrices.

It is an object of the present invention to provide novel organic fluorescent dyes. The fluorescent dyes should have at least one of the following properties:
high photostability,
high fluorescence quantum yield in polymeric matrices,
high compatibility with the LED production operation,
use as a radiation conversion luminophore in place of YAG doped with rare earths, especially Ce:YAG, and improvement of the color rendering index of the light source in combination with further red-emitting fluorescent dyes.

The object is surprisingly achieved by the cyanated perylene compounds of the formula I described below:

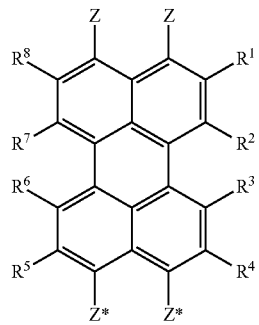

(I)

in which
one of the Z substituents is cyano and the other Z substituent is $CO_2R^9$, $CONR^{10}R^{11}$, $C_1$-$C_{18}$-alkyl, $C_2$-$C_{18}$-alkenyl, $C_2$-$C_{18}$-alkynyl, $C_3$-$C_{12}$-cycloalkyl or $C_6$-$C_{14}$-aryl, where
$C_1$-$C_{18}$-alkyl, $C_2$-$C_{18}$-alkenyl, $C_2$-$C_{18}$-alkynyl are unsubstituted or bear one or more identical or different $Z^a$ substituents,
$C_3$-$C_{12}$-cycloalkyl is unsubstituted or bears one or more identical or different $Z^b$ substituents, and
$C_6$-$C_{14}$-aryl is unsubstituted or bears one or more identical or different $Z^{Ar}$ substituents;
one of the Z* substituents is cyano and the other Z* substituent is $CO_2R^9$, $CONR^{10}R^{11}$, $C_1$-$C_{18}$-alkyl, $C_2$-$C_{18}$-alkenyl, $C_2$-$C_{18}$-alkynyl, $C_3$-$C_{12}$-cycloalkyl or $C_6$-$C_{14}$-aryl, where
$C_1$-$C_{18}$-alkyl, $C_2$-$C_{18}$-alkenyl, $C_2$-$C_{18}$-alkynyl are unsubstituted or bear one or more identical or different $Z^a$ substituents,
$C_3$-$C_{12}$-cycloalkyl is unsubstituted or bears one or more identical or different $Z^b$ substituents, and
$C_6$-$C_{14}$-aryl is unsubstituted or bears one or more identical or different $Z^{Ar}$ substituents;

$R^1$, $R^2$, $R^3$, $R^4$, $R^5$, $R^6$, $R^7$ and $R^8$ are each independently selected from hydrogen, cyano, bromine and chlorine, with the proviso that 1, 2, 3, 4, 5, 6, 7 or 8 of the $R^1$, $R^2$, $R^3$, $R^4$, $R^5$, $R^6$, $R^7$ or $R^8$ substituents are cyano;
where
$R^9$ is hydrogen, $C_1$-$C_{10}$-alkyl, $C_2$-$C_{10}$-alkenyl, $C_2$-$C_{10}$-alkynyl, $C_3$-$C_{12}$-cycloalkyl or $C_6$-$C_{14}$-aryl, where
$C_1$-$C_{10}$-alkyl, $C_2$-$C_{10}$-alkenyl, $C_2$-$C_{10}$-alkynyl are unsubstituted or bear one or more identical or different $R_a$ substituents, $C_3$-$C_{12}$-cycloalkyl is unsubstituted or bears one or more identical or different $R^b$ substituents and $C_6$-$C_{14}$-aryl is unsubstituted or bears one or more identical or different $R^{Ar}$ substituents;
$R^{10}$ and $R^{11}$ are each independently hydrogen, $C_1$-$C_{10}$-alkyl, $C_2$-$C_{10}$-alkenyl, $C_2$-$C_{10}$-alkynyl, $C_3$-$C_{12}$-cycloalkyl or $C_6$-$C_{14}$-aryl, where
$C_1$-$C_{10}$-alkyl, $C_2$-$C_{10}$-alkenyl, $C_2$-$C_{10}$-alkynyl are unsubstituted or bear one or more identical or different $R_a$ substituents, $C_3$-$C_{12}$-cycloalkyl is unsubstituted or bears one or more identical or different $R^b$ substituents and $C_4$-$C_{14}$-aryl is unsubstituted or bears one or more identical or different $R^{Ar}$ substituents;
each $Z^a$ is independently halogen, hydroxyl, $NR^{10a}R^{11a}$, $C_1$-$C_{10}$-alkoxy, $C_1$-$C_{10}$-haloalkoxy, $C_1$-$C_{10}$-alkylthio, $C_3$-$C_{12}$-cycloalkyl, $C_6$-$C_{14}$-aryl, $C(=O)R^{9a}$, $C(=O)OR^{9a}$ or $C(O)NR^{10a}R^{11a}$, where
$C_3$-$C_{12}$-cycloalkyl is unsubstituted or bears one or more identical or different $R^b$ substituents and
$C_6$-$C_{14}$-aryl is unsubstituted or bears one or more identical or different $R^{Ar}$ substituents;
each $Z^b$ and each $Z^{Ar}$ is independently halogen, hydroxyl, $NR^{10a}R^{11a}$, $C_1$-$C_{10}$-alkyl, $C_1$-$C_{10}$-alkoxy, $C_1$-$C_{10}$-haloalkoxy, $C_1$-$C_{10}$-alkylthio, $C(=O)R^{9a}$, $C(=O)OR^{9a}$ or $C(O)NR^{10a}R^{11a}$;
each $R^a$ is independently halogen, hydroxyl, $C_1$-$C_{10}$-alkoxy, $C_3$-$C_{12}$-cycloalkyl or $C_6$-$C_{14}$-aryl;
each $R^b$ is independently halogen, hydroxyl, $C_1$-$C_{10}$-alkyl, $C_1$-$C_{10}$-alkoxy, $C_1$-$C_{10}$-haloalkoxy, $C_1$-$C_{10}$-alkylthio, $C_2$-$C_{10}$-alkenyl, $C_2$-$C_{10}$-alkynyl, $C_3$-$C_{12}$-cycloalkyl or $C_6$-$C_{14}$-aryl;
each $R^{Ar}$ is independently halogen, hydroxyl, $C_1$-$C_{10}$-alkyl, $C_1$-$C_{10}$-alkoxy, $C_1$-$C_{10}$-haloalkoxy, $C_1$-$C_{10}$-alkylthio, $C_2$-$C_{10}$-alkenyl, $C_2$-$C_{10}$-alkynyl, $C_3$-$C_{12}$-cycloalkyl or $C_6$-$C_{14}$-aryl;
$R^{9a}$ is hydrogen, $C_1$-$C_{10}$-alkyl, $C_2$-$C_{10}$-alkenyl, $C_2$-$C_{10}$-alkynyl, $C_3$-$C_{12}$-cycloalkyl or $C_6$-$C_{14}$-aryl; and
$R^{10a}$, $R^{11a}$ are each independently hydrogen, $C_1$-$C_{10}$-alkyl, $C_2$-$C_{10}$-alkenyl, $C_2$-$C_{10}$-alkynyl, $C_3$-$C_{12}$-cycloalkyl or $C_6$-$C_{14}$-aryl;
and mixtures thereof.

The present invention likewise provides a composition comprising at least one cyanated perylene compound of the formula I as defined above or mixtures thereof and processes for preparation thereof.

The present invention likewise provides for the use of the cyanated perylene compound of the formula I as defined above and mixtures thereof or of a composition comprising at least one cyanated perylene compound of the formula I as defined above and mixtures thereof in color converters, for optical labels, for invisible marking of products, as fluorescent dyes, preferably as fluorescent labels for biomolecules, as pigments, as a fluorescent dye in a display based on fluorescence conversion; in a light-collecting plastics part optionally combined with a solar cell; as a pigment dye in electrophoretic displays; as a fluorescent dye in an application based on chemoluminescence.

The present invention further provides color converters comprising at least one polymer as matrix and at least one cyanated perylene compound of the formula I as defined above or mixtures thereof or a composition comprising at least one cyanated perylene compound of the formula I as defined above and mixtures thereof as a fluorescent dye.

The present invention further provides for the use of the color converters for conversion of light generated by LEDs.

The present invention further provides a lighting device comprising at least one LED and at least one color converter as defined above.

The inventive cyanated perylene compounds of the formula I and mixtures thereof are surprisingly photostable and can be used advantageously in a color converter for blue LEDs. In addition, the inventive cyanated perylene compounds of the formula I and mixtures thereof have a high fluorescence quantum yield in polymeric matrices. They have high compatibility with the LED production process. The inventive cyanated perylene compounds of the formula I and mixtures thereof are suitable, in combination with red-emitting fluorescent dyes, especially for color converters in blue-emitting LEDs for production of light sources having a CRI above 90. Surprisingly, the novel fluorescent dyes are also suitable as alternative radiation conversion luminophores for Ce:YAG, and so white LEDs not comprising any rare earths as a luminophore are obtainable.

The definitions of the variables specified in the above formulae use collective terms which are generally representative of the respective substituents. The definition $C_n$-$C_m$ gives the number of carbon atoms possible in each case in the respective substituent or substituent moiety:

Halogen: fluorine, chlorine, bromine or iodine.

Alkyl and alkyl moieties in alkoxy and alkylthio: saturated straight-chain or branched hydrocarbyl radicals having 1 to 30 ($C_1$-$C_{30}$-alkyl), frequently 1 to 20 ($C_1$-$C_{20}$-alkyl) and especially 1 to 10 ($C_1$-$C_{10}$-alkyl) carbon atoms, such as methyl, ethyl, propyl, 1-methyl-ethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl, heptyl, 1-methyl-hexyl, octyl, 1-methylheptyl, 2-ethylhexyl, n-nonyl, n-decyl.

Haloalkyl and all haloalkyl moieties in haloalkoxy: straight-chain or branched alkyl groups having 1 to 30, frequently 1 to 20 and especially 1 to 10 carbon atoms (as specified above), where some or all of the hydrogen atoms in these groups may be replaced by halogen atoms as specified above.

The term "alkylene" encompasses, in principle, straight-chain or branched radicals having 1 to 10 carbon atoms, such as methylene, 1,1-ethylene, 1,2-ethylene, prop-1,2-ylene, prop-1,3-ylene, but-1,2-ylene, but-1,3-ylene, but-1,4-ylene, 2-methylprop-1,3-ylene, pent-1,2-ylene, pent-1,3-ylene, pent-1,4-ylene, pent-1,5-ylene, pent-2,3-ylene, pent-2,4-ylene, 1-methylbut-1,4-ylene, 2-methylbut-1,4-ylene, hex-1,3-ylene, hex-2,4-ylene, hex-1,4-ylene, hex-1,5-ylene, hex-1,6-ylene and the like.

Alkenyl: monounsaturated straight-chain or branched hydrocarbyl radicals having 2 to ($C_2$-$C_{10}$-alkenyl), for example 2 to 10 or 3 to 10, carbon atoms and one double bond in any position, for example ethenyl, 1-propenyl, 2-propenyl, 1-methylethenyl, 1-butenyl, 2-butenyl, 3-bute- nyl, 1-methyl-1-propenyl, 2-methyl-1-propenyl, 1-methyl-2-propenyl, 2-methyl-2-propenyl.

Alkynyl: straight-chain or branched hydrocarbyl groups having 2 to 10 ($C_2$-$C_{10}$-alkynyl), for example 2 to 10 or 3 to 10, carbon atoms and a triple bond in any position, for example ethynyl, 1-propynyl, 2-propynyl, 1-butynyl, 2-butynyl, 3-butynyl, 1-methyl-2-propynyl.

Cycloalkyl: monocyclic, bicyclic or tricyclic saturated hydrocarbyl group having 3 to 12 carbon ring members, for example monocyclic $C_3$-$C_8$-cycloalkyl such as cyclopropyl, cyclobutyl, cyclopentyl, cyclohexyl, cycloheptyl, cyclooctyl, bicyclic $C_7$-$C_{12}$-cycloalkyl such as bicyclo[2.2.1]hept-1-yl, bicyclo[2.2.1]hept-2-yl, bicyclo[2.2.1]hept-7-yl, bicyclo[2.2.2]oct-1-yl, bicyclo[2.2.2]oct-2-yl and bicyclo[3.3.0]octyl, and tricyclic $C_{10}$-$C_{12}$-cycloalkyl such as tricyclo[3.3.1.1$^{3,7}$]decanyl.

Aryl: mono-, di- or trinuclear (monocyclic, bicyclic or tricyclic) aromatic hydrocarbyl radicals having 6 to 14 and more preferably 6 to 10 carbon atoms, which do not comprise any ring heteroatoms. Examples of aryl are especially phenyl, naphthyl, indenyl, fluorenyl, anthracenyl, phenanthrenyl, and specifically phenyl or naphthyl.

$C_6$-$C_{14}$-Aryl-$C_1$-$C_{10}$-alkylene: $C_6$-$C_{14}$-aryl as defined above, which is bonded to the skeleton via $C_1$-$C_{10}$-alkylene, as defined above. Examples thereof are phenyl-$C_1$-$C_{10}$-alkylene (phenyl-$C_1$-$C_{10}$-alkyl) and naphthyl-$C_1$-$C_{10}$-alkylene (naphthyl-$C_1$-$C_{10}$-alkyl) and specifically phenyl-$C_1$-$C_4$-alkyl such as benzyl or 2-phenylethyl.

$C_6$-$C_4$-Aryloxy: $C_6$-$C_{14}$-aryl as defined above, which is bonded to the skeleton via an oxygen atom (—O—). Preference is given to phenoxy and naphthyloxy.

Heteroaryl (hetaryl): mono-, bi- or trinuclear (monocyclic, bicyclic or tricyclic) aromatic ring system having 5 to 14 ring members, comprising, as well as carbon atoms as ring members, generally 1, 2, 3 or 4 heteroatoms as ring members, selected from oxygen, sulfur and nitrogen such as:

five- or six-membered aromatic heterocycle comprising one, two, three or four heteroatoms from the group of oxygen, nitrogen and sulfur: for example C-bonded 5-membered heteroaryl comprising one to three nitrogen atoms or one or two nitrogen atoms and/or one sulfur or oxygen atom as ring members, such as 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl and 1,3,4-triazol-2-yl; nitrogen-bonded 5-membered heteroaryl comprising one to three nitrogen atoms as ring members, such as pyrrol-1-yl, pyrazol-1-yl, imidazol-1-yl, 1,2,3-triazol-1-yl and 1,2,4-triazol-1-yl; 6-membered heteroaryl comprising one to three nitrogen atoms as ring members, such as pyridin-2-yl, pyridin-3-yl, pyridin-4-yl, 3-pyridazinyl, 4-pyridazinyl, 2-pyrimidinyl, 4-pyrimidinyl, 5-pyrimidinyl, 2-pyrazinyl, 1,3,5-triazin-2-yl and 1,2,4-triazin-3-yl;

benzofused five- or six-membered aromatic heterocycle comprising one, two, three or four, preferably one, two or three heteroatoms from the group of oxygen, nitrogen and sulfur: for example five- or six-membered aromatic heterocycles, as defined above, which may comprise, as well as carbon atoms, one to four nitrogen atoms or one to three nitrogen atoms and one sulfur or oxygen atom as ring members, and in which two adjacent carbon ring members or one nitrogen and one adjacent carbon ring member may be bridged by a buta-1,3-diene-1,4-diyl group, such as indolyl, indazolyl, benzofuryl, dibenzofuryl, isobenzofuranyl, benzothiophenyl, dibenzothiophenyl, benzothiazolyl, benzoxazolyl, benzimidazolyl, carbazolyl, quinolinyl, isoquinolinyl, quinazolinyl, quinoxalinyl, cinnolinyl, phthalazinyl, purinyl, acridinyl, phenanthridinyl, phenazinyl and 1,7-phenanthrolinyl.

In the context of the present invention, a "blue LED" is understood to mean an LED which emits light in the wavelength range from 400 to 500 nm, preferably 420 to 480 nm and especially 440 to 460 nm. Suitable semiconductor materials are silicon carbide, zinc selenide and nitrides such as aluminum nitride (AlN), gallium nitride (GaN), indium nitride (InN) and indium gallium nitride (InGaN). In the context of the present invention, a "white LED" is understood to mean an LED which produces white light. Examples of a white LED are multi-LEDs or a blue LED in combination with at least one radiation conversion luminophore.

In the context of the present invention, "color converter" is understood to mean all physical devices capable of absorbing light of particular wavelengths and converting it to light of other wavelengths. Color converters are, for example, part of lighting devices, especially those lighting devices which utilize LEDs or OLEDs as a light source, or of fluorescence conversion solar cells.

The word "essentially" in the context of the present invention encompasses the words "completely", "wholly" and "all". The word encompasses a proportion of 90% or more, such as 95% or more, specifically 99% or 100%.

The details which follow in relation to preferred embodiments of the Z, Z*, $R^1$, $R^2$, $R^3$, $R^4$, $R^5$, $R^6$, $R^7$ and $R^8$ substituents (radicals) in the perylene compounds of the formula I apply independently to each substituent, and likewise in combination of the substituents with one another.

The details which follow in relation to preferred embodiments of the Z, Z*, $R^1$, $R^2$, $R^3$, $R^4$, $R^5$, $R^6$, $R^7$ and $R^8$ substituents additionally apply to the perylene compounds of the formula I, and also to the use thereof in color converters and lighting devices.

In the inventive perylene compounds of the formula I and mixtures thereof, one of the Z substituents and one of the Z* substituents are cyano and the other Z substituent and the other Z* substituent in each case is different than cyano. The present invention encompasses both the compound of the formula I individually and mixtures thereof.

The present invention especially encompasses the following compounds of the formulae I-a and I-b, and also I-c and I-d:

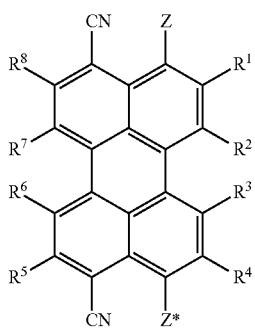
(I-a)

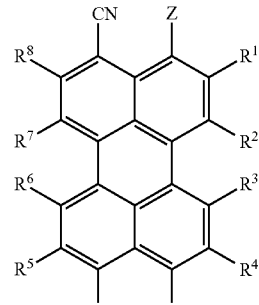
(I-b)

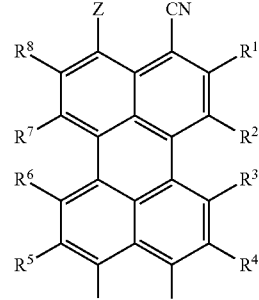
(I-c)

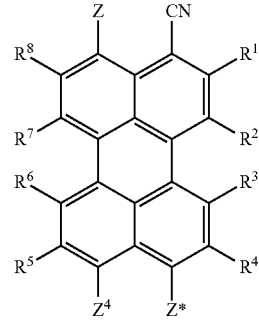
(I-d)

in which
$R^1$, $R^2$, $R^3$, $R^4$, $R^5$, $R^6$, $R^7$, $R^8$, Z and Z* are each as defined above, individually and mixtures thereof. More particularly, in compounds of the formulae I-a, I-b, I-c and I-d, the $R^1$, $R^2$, $R^3$, $R^4$, $R^5$, $R^6$, $R^7$, $R^8$ substituents that are not cyano or hydrogen are all chlorine or all bromine.

In the inventive perylene compounds of the formula I and mixtures thereof, 1, 2, 3, 4, 5, 6, 7 or 8 of the $R^1$, $R^2$, $R^3$, $R^4$, $R^5$, $R^6$, $R^7$ and $R^8$ substituents are cyano. The other $R^1$, $R^2$, $R^3$, $R^4$, $R^5$, $R^6$, $R^7$ and $R^8$ substituents are each independently hydrogen, bromine or chlorine. More particularly, the other $R^1$, $R^2$, $R^3$, $R^4$, $R^5$, $R^6$, $R^7$ and $R^8$ substituents are each independently hydrogen or bromine. In a further embodiment, the other $R^1$, $R^2$, $R^3$, $R^4$, $R^5$, $R^6$, $R^7$ and $R^8$ substituents are each independently hydrogen or chlorine.

In a first preferred embodiment, 1, 2, 3 or 4 of the $R^1$, $R^2$, $R^3$, $R^4$, $R^5$, $R^6$, $R^7$ and $R^8$ substituents are cyano. The other $R^1$, $R^2$, $R^3$, $R^4$, $R^5$, $R^6$, $R^7$ and $R^8$ substituents are each independently hydrogen, bromine or chlorine. Specifically, 1, 2, 3 or 4 of the $R^2$, $R^3$, $R^6$ and $R^7$ substituents are cyano. In a specific embodiment, none of the $R^1$, $R^2$, $R^3$, $R^4$, $R^5$, $R^6$, $R^7$ or $R^8$ substituents is bromine or chlorine.

In a second preferred embodiment, one of the $R^1$, $R^2$, $R^3$, $R^4$, $R^5$, $R^6$, $R^7$ and $R^8$ substituents is cyano, and the other $R^1$, $R^2$, $R^3$, $R^4$, $R^5$, $R^6$, $R^7$ and $R^8$ substituents are hydrogen. In particular, one of the R², R³, R⁶ and R⁷ substituents is cyano, and the other R¹, R², R³, R⁴, R⁵, R⁶, R⁷ and R⁸ substituents are hydrogen.

In a third preferred embodiment, two of the R¹, R², R³, R⁴, R⁵, R⁶, R⁷ and R⁸ substituents are cyano, and the other R¹, R², R³, R⁴, R⁵, R⁶, R⁷ and R⁸ substituents are hydrogen. In particular, two of the R², R³, R⁶ and R⁷ substituents are cyano, and the other R¹, R², R³, R⁴, R⁵, R⁶, R⁷ and R⁸ substituents are hydrogen.

In the inventive perylene compounds of the formula I and mixtures thereof, one of the Z substituents is cyano and one of the Z* substituents is cyano. The other Z substituent and the other Z* substituent are each as defined above and are preferably selected independently from $C_1$-$C_{10}$-alkyl, $CO_2R^9$, phenyl-$C_1$-$C_{10}$-alkyl and phenyl, where phenyl and the phenyl moiety of phenyl-$C_1$-$C_{10}$-alkyl are unsubstituted or bear one or more, for example 1, 2 or 3, substituents selected from $C_1$-$C_6$-alkyl, and where $R^9$ is as defined above. Preferably, $R^9$ is linear or branched $C_1$-$C_6$-alkyl, specifically methyl, ethyl, n-propyl, isopropyl, n-butyl or isobutyl.

Even more preferably, one of the Z substituents is $C_1$-$C_6$-alkyl, $C_1$-$C_6$-alkoxycarbonyl or phenyl which is unsubstituted or bears 1, 2 or 3 $C_1$-$C_4$-alkyl groups. Specifically, one of the Z substituents is $C_1$-$C_6$-alkyl such as methyl, ethyl, n-propyl, isopropyl, n-butyl, isobutyl, $C_1$-$C_6$-alkoxycarbonyl such as methoxycarbonyl, ethoxycarbonyl, n-propoxycarbonyl, isopropoxycarbonyl, n-butoxycarbonyl, isobutoxycarbonyl, phenyl, or phenyl bearing 1, 2 or 3 $C_1$-$C_4$-alkyl groups, such as 2-methylphenyl or 2,6-dimethylphenyl.

Even more preferably, one of the Z* substituents is $C_1$-$C_6$-alkyl, $C_1$-$C_6$-alkoxycarbonyl or phenyl which is unsubstituted or bears 1, 2 or 3 $C_1$-$C_4$-alkyl groups. Specifically, one of the Z* substituents is $C_1$-$C_6$-alkyl such as methyl, ethyl, n-propyl, isopropyl, n-butyl, isobutyl, $C_1$-$C_6$-alkoxycarbonyl such as methoxycarbonyl, ethoxycarbonyl, n-propoxycarbonyl, isopropoxycarbonyl, n-butoxycarbonyl, isobutoxycarbonyl, phenyl, 2-methylphenyl or 2,6-dimethylphenyl.

In a particularly preferred embodiment, the perylene compound of the formula I is selected from compounds of the formulae (1), (2), (3), (4), (5), (6), (7), (8), (9), (10), (11), (12), (13), (14), (15), (16), (17), (18), (19), (20)

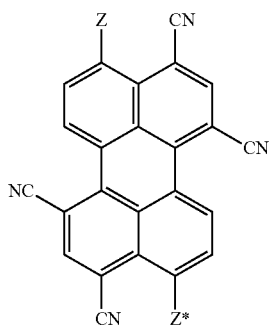

(1)

-continued

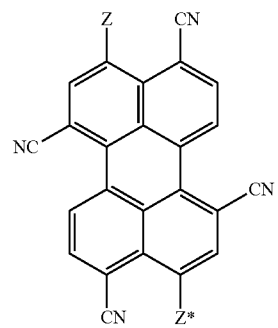

(2)

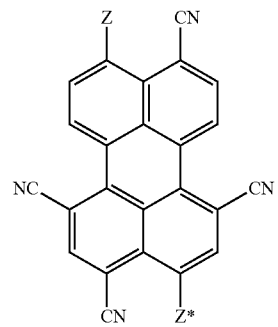

(3)

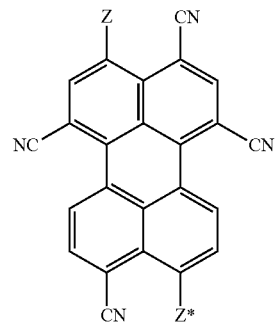

(4)

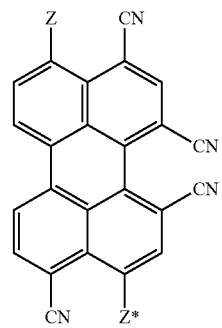

(5)

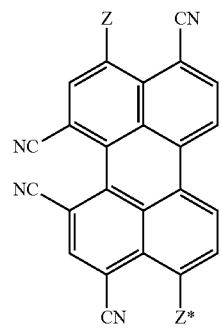

(6)

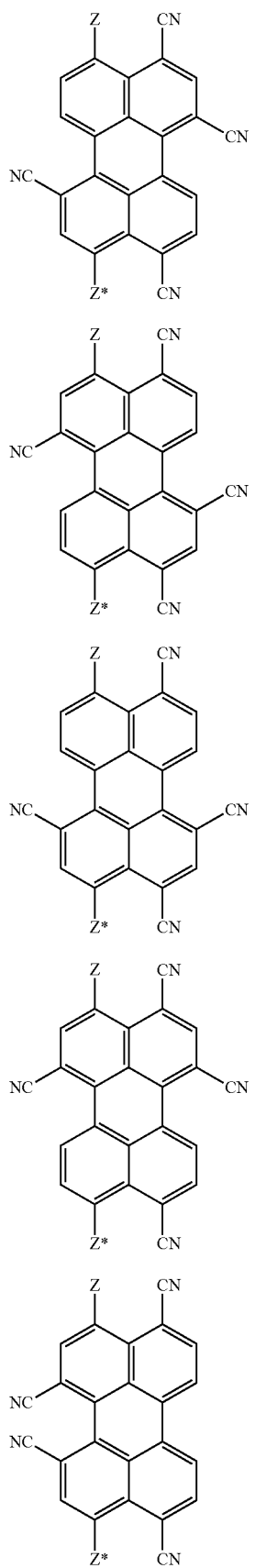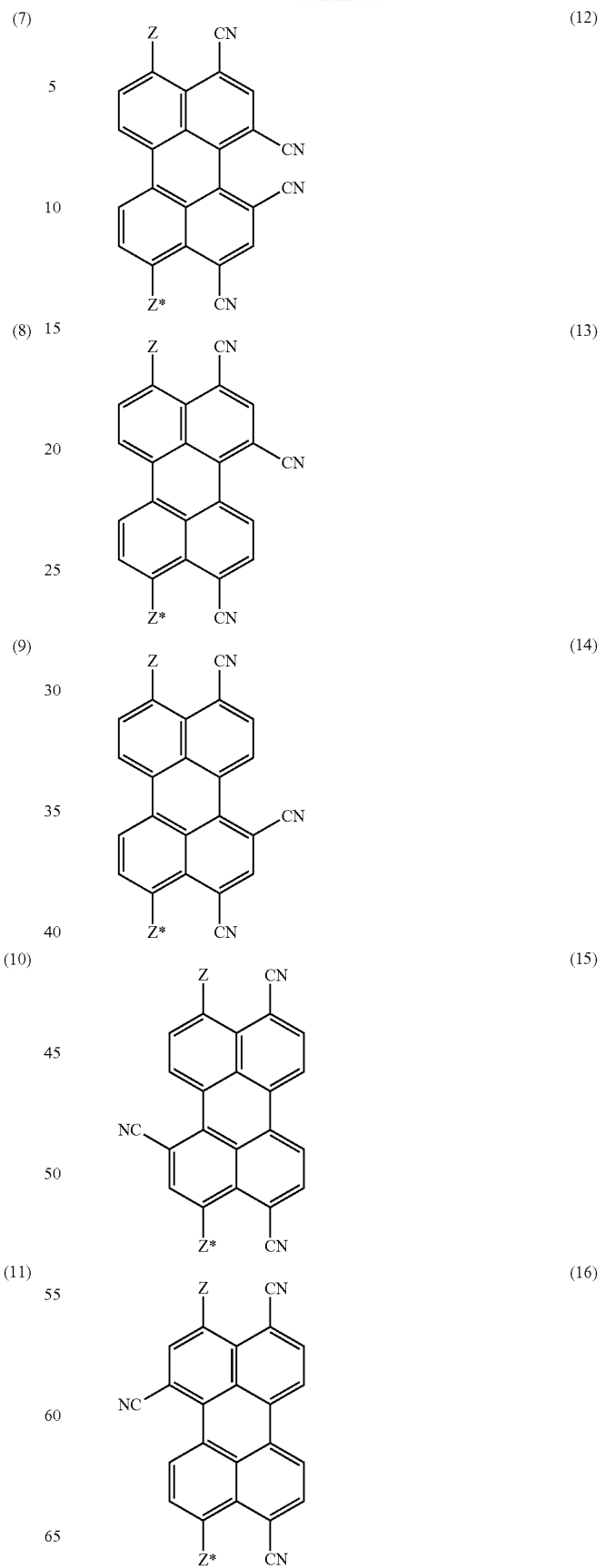

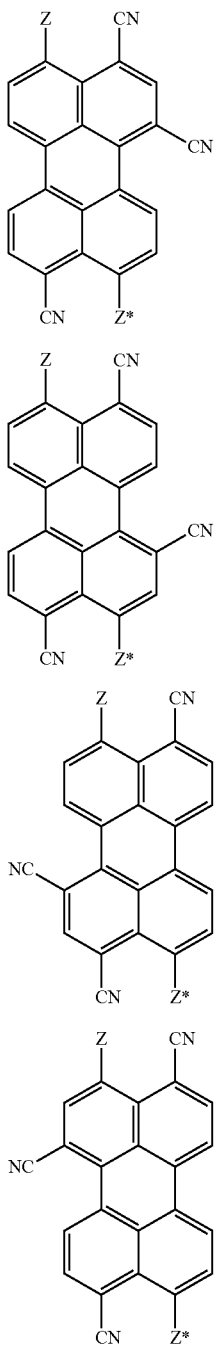

in which
Z is selected from $C_1$-$C_6$-alkyl, $C_1$-$C_6$-alkoxycarbonyl, phenyl, and phenyl bearing 1, 2 or 3 $C_1$-$C_4$-alkyl groups; and
Z* Is selected from $C_1$-$C_6$-alkyl, $C_1$-$C_6$-alkoxycarbonyl, phenyl, and phenyl bearing 1, 2 or 3 $C_1$-$C_4$-alkyl groups;
and mixtures thereof.

Among these, specific preference is given to perylene compounds of the formulae (1), (2), (3), (4), (5), (6), (7), (8), (9), (10), (11), (12), (13), (14), (15), (16), (17), (18), (19), (20) in which Z and Z* have the same definition.

The present invention further provides a composition comprising at least one cyanated perylene compound of the formula I as defined above or mixtures thereof.

The perylene compounds of the formula I and mixtures thereof can be prepared by processes known to those skilled in the art or as described hereinafter.

The invention further provides a composition comprising at least one cyanated perylene compound of the formula I-A

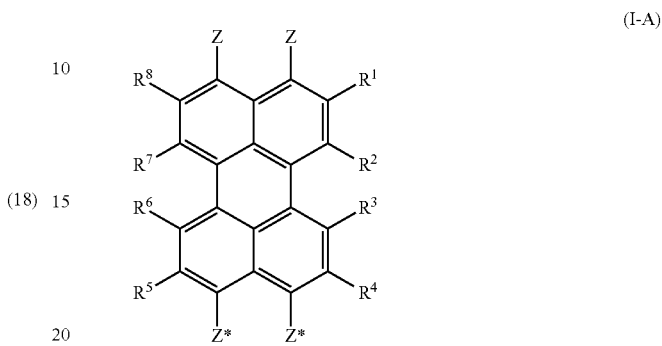

in which
one of the Z substituents is cyano and the other Z substituent is $C_1$-$C_{18}$-alkyl, $C_2$-$C_{18}$-alkenyl, $C_2$-$C_{18}$-alkynyl, $C_3$-$C_{12}$-cycloalkyl or $C_6$-$C_{14}$-aryl, where
  $C_1$-$C_{18}$-alkyl, $C_2$-$C_{18}$-alkenyl, $C_2$-$C_{18}$-alkynyl are unsubstituted or bear one or more identical or different $Z^a$ substituents, where $Z^a$ is as defined above;
  $C_3$-$C_{12}$-cycloalkyl is unsubstituted or bears one or more identical or different $Z^b$ substituents, where $Z^b$ is as defined above; and
  $C_6$-$C_{14}$-aryl is unsubstituted or bears one or more identical or different $Z^{Ar}$ substituents, where $Z^{Ar}$ is as defined above;
one of the Z* substituents is cyano and the other Z* substituent is $C_1$-$C_{18}$-alkyl, $C_2$-$C_{18}$-alkenyl, $C_2$-$C_{18}$-alkynyl, $C_3$-$C_{12}$-cycloalkyl or $C_6$-$C_{14}$-aryl, where
  $C_1$-$C_{18}$-alkyl, $C_2$-$C_{18}$-alkenyl, $C_2$-$C_{18}$-alkynyl are unsubstituted or bear one or more identical or different $Z^a$ substituents, where $Z^a$ is as defined above;
  $C_3$-$C_{12}$-cycloalkyl is unsubstituted or bears one or more identical or different $Z^b$ substituents, where $Z^b$ is as defined above; and
  $C_6$-$C_{14}$-aryl is unsubstituted or bears one or more identical or different $Z^{Ar}$ substituents, where $Z^{Ar}$ is as defined above;
$R^1$, $R^4$, $R^5$ and $R^8$ are each hydrogen;
two of the $R^2$, $R^3$, $R^6$ or $R^7$ substituents are hydrogen; and the other $R^2$, $R^3$, $R^6$ or $R^7$ substituents are cyano;
or mixtures thereof,
obtainable by a process in which
a) perylene of the formula II

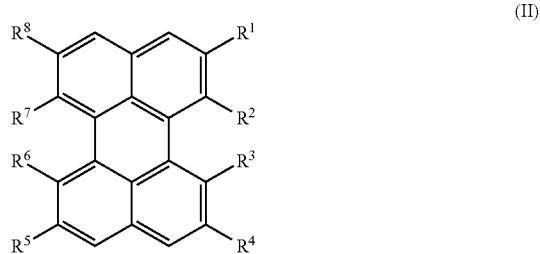

in which

R$^1$, R$^2$, R$^3$, R$^4$, R$^5$, R$^6$, R$^7$ and R$^8$ are each hydrogen is halogenated to obtain a mixture of 3,9-dihaloperylene of the formula IIIa and 3,10-dihaloperylene of the formula IIIb

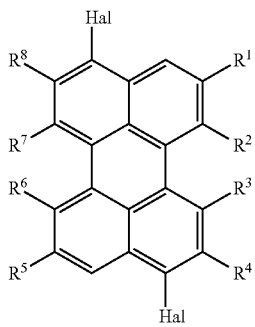

(IIIa)

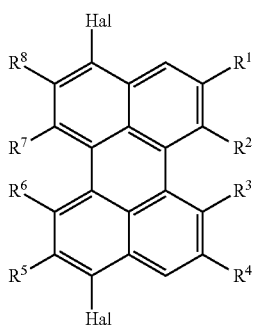

(IIIb)

in which

R$^1$, R$^2$, R$^3$, R$^4$, R$^5$, R$^6$, R$^7$ and R$^8$ are each hydrogen; and
Hal are each all chlorine or bromine;

b) the mixture of compounds of the formulae IIIa and IIIb obtained in step a) is reacted with an organometallic compound of the formula IV Z-Met                 (IV)

and optionally with an organometallic compound of the formula V

Z*-Met                 (V)

in which

Z is selected from C$_1$-C$_{18}$-alkyl, C$_2$-C$_{18}$-alkenyl, C$_2$-C$_{18}$-alkynyl, C$_3$-C$_{12}$-cycloalkyl and C$_8$-C$_{14}$-aryl, where C$_1$-C$_{18}$-alkyl, C$_2$-C$_{18}$-alkenyl, C$_2$-C$_{18}$-alkynyl are unsubstituted or bear one or more identical or different Z$^a$ substituents, C$_3$-C$_{12}$-cycloalkyl is unsubstituted or bears one or more identical or different Z$^b$ substituents, and C$_6$-C$_{14}$-aryl is unsubstituted or bears one or more identical or different Z$^{Ar}$ substituents;

Z* is selected from C$_1$-C$_{18}$-alkyl, C$_2$-C$_{18}$-alkenyl, C$_2$-C$_{18}$-alkynyl, C$_3$-C$_{12}$-cycloalkyl and C$_6$-C$_{14}$-aryl, where C$_1$-C$_{18}$-alkyl, C$_2$-C$_{18}$-alkenyl, C$_2$-C$_{18}$-alkynyl are unsubstituted or bear one or more identical or different Z$^a$ substituents, C$_3$-C$_{12}$-cycloalkyl is unsubstituted or bears one or more identical or different Z$^b$ substituents, and C$_6$-C$_{14}$-aryl is unsubstituted or bears one or more identical or different Z$^{Ar}$ substituents;

where Z* may also be as defined for Z;

Met is B(OH)$_2$, B(OR')(OR''), Zn-Hal or Sn(R*)$_3$, in which

R' and R'' are each independently hydrogen, C$_1$-C$_{30}$-alkyl, C$_5$-C$_8$-cycloalkyl, C$_6$-C$_{14}$-aryl or heteroaryl, or R' and R'' together are C$_2$-C$_4$-alkylene which optionally bears 1, 2, 3, 4, 5, 6, 7 or 8 substituents selected from C$_1$-C$_4$-alkyl, C$_5$-C$_8$-cycloalkyl, C$_6$-C$_{14}$-aryl and heteroaryl;

Hal is chlorine or bromine; and

R* is C$_1$-C$_8$-alkyl or phenyl, to obtain a mixture of compounds of the formulae VIa and VIb,

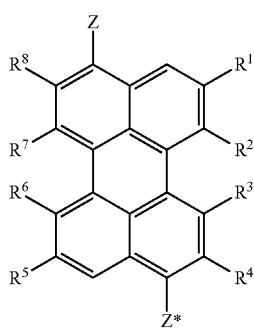

(VIa)

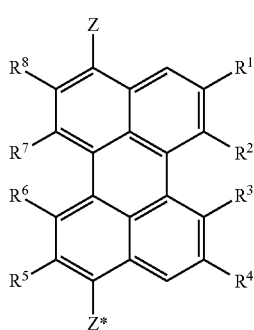

(VIb)

in which

R$^1$, R$^2$, R$^3$, R$^4$, R$^5$, R$^6$, R$^7$ and R$^8$ are each hydrogen; and
Z and Z* are each as defined above;

c) the mixture of compounds of the formulae VIa and VIb obtained in step b) is halogenated to obtain a reaction mixture comprising compounds of the formulae VIIa and VIIb

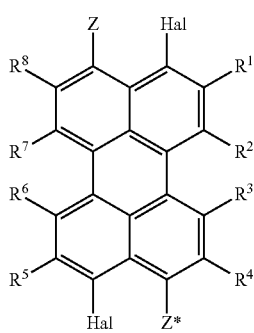

(VIIa)

-continued

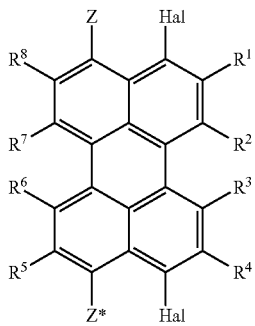

(VIIb)

in which

Z and Z* are each as defined above;

Hal is halogen selected from chlorine and bromine, where the Hal substituents are either all chlorine or all bromine, $R^1$, $R^2$, $R^3$, $R^4$, $R^5$, $R^6$, $R^7$ and $R^8$ are each hydrogen or halogen selected from chlorine and bromine, where the $R^1$, $R^2$, $R^3$, $R^4$, $R^5$, $R^6$, $R^7$ and $R^8$ substituents that are not hydrogen are either all chlorine or all bromine;

d) the compounds of the formulae VIIa and VIIb present in the reaction mixture obtained in step c) are subjected to a substitution of halogen for cyano, and optionally partly for hydrogen, to obtain at least one compound of the formula I-A or mixtures thereof; and e) the at least one compound of the formula I-A or mixtures thereof present in the reaction mixture obtained in step d) is optionally subjected to at least one separation and/or purification step.

Step a)

The halogenation of perylene of the formula II is effected typically with a brominating agent or a chlorinating agent, meaning that either all the Hal substituents in the compounds of the formulae IIIa or IIIb are bromine or all the Hal substituents are chlorine.

Typically, elemental bromine in a solvent is used as the brominating agent. Further suitable brominating agents are N-bromosuccinimide and dibromoisocyanuric acid. Suitable solvents are water or aliphatic monocarboxylic acids, and chlorinated hydrocarbons such as chlorobenzene and chloroform. Suitable aliphatic monocarboxylic acids are those having 2 to 6 carbon atoms, such as acetic acid, propionic acid, butyric acid, pentanecarboxylic acid and hexanecarboxylic acid, and mixtures thereof. When an aliphatic monocarboxylic acid is used as a solvent, it may be advantageous to use iodine as a catalyst.

Suitable chlorinating agents are chlorine in a solvent, e.g. tetrachloromethane. Likewise suitable are N-chlorosuccinimide and dichloroisocyanuric acid. Chlorination with dichloroisocyanuric acid is effected preferably in concentrated sulfuric acid.

The molar ratio of brominating agent to perylene of the formula II is typically about 10:1 to 2.5:1, more preferably 9:1 to 3.0:1. The molar ratio is especially 8.5:1 to 3.5:1.

The molar ratio of chlorinating agent to perylene of the formula II is typically about 10:1 to 2.5:1, more preferably 9:1 to 3.0:1. The molar ratio is especially 8.5:1 to 3.5:1.

The dihalogenated compounds of the formulae IIIa and IIIb obtained in reaction step a) are generally used in step b) without further purification.

Step b)

In the reaction in step b), the compounds of the formulae IIIa and IIIb obtained in step a) are subjected to a cross-coupling with an organometallic compound of the formula IV and optionally with an organometallic compound of the formula V.

Preference is given to effecting the reaction in the presence of catalytically active amounts of a transition metal of transition group VIII of the Periodic Table (group 10 according to IUPAC), for example nickel, palladium or platinum, especially in the presence of a palladium catalyst. Suitable catalysts are, for example, palladium-phosphine complexes such as tetrakis(triphenylphosphine)palladium(0), $PdCl_2$(o-tolyl$_3$P)$_2$, bis(triphenylphosphine)palladium(II) chloride, the [1,1'-bis(diphenylphosphino)ferrocene]palladium(II) chloride-dichloromethane complex, bis[1,2-bis(diphenylphosphino)ethane]palladium(0) and [1,4-bis(diphenylphosphino)butane]palladium(II) chloride, palladium on activated carbon in the presence of phosphine compounds, and palladium(II) compounds such as palladium(II) chloride or bis(acetonitrile)palladium(II) chloride in the presence of phosphine compounds such as triphenylphosphine, 1,1'-bis(diphenylphosphino)ferrocene, 1,2-bis(diphenylphosphino)ethane, 1,3-bis(diphenylphosphino)propane and 1,4-bis(diphenylphosphino)butane. The amount of catalyst is typically 10 to 150 mol %, based on the compounds of the formulae IIIa and IIIb.

Especially suitable organometallic compounds IV are an appropriately substituted arylboronic acid and arylboronic esters (compounds IV where Met=B(OH)$_2$ or B(OR')(OR'') where R', R''=C$_1$-C$_4$-alkyl, or R' and R'' together are C$_2$-C$_4$-alkylene optionally bearing 1, 2, 3 or 4 substituents selected from C$_1$-C$_4$-alkyl).

The reaction is effected under the conditions of a Suzuki coupling, as known, for example, from Suzuki et al., Chem. Rev., 1995, 95, 2457-2483 and the literature cited therein. The arylboronic acids and esters thereof are known from the literature, commercially available, or can be prepared from the corresponding arylmagnesium compounds by reaction with appropriate boric esters. Suitable organometallic compounds IV are additionally alkylboronic acid or alkylboronic esters.

Suitable organometallic compounds IV are especially also arylstannanes, cycloalkylstannanes, alkynylstannanes, alkenylstannanes or alkylstannanes (compounds IV where Met=Sn(R*)$_3$ where R*=C$_1$-C$_4$-alkyl). In that case, the reaction is effected under the conditions of a Stille coupling, as known, for example, from D. Milstein, J. K. Stille, J. Am. Chem. Soc. 1978, 100, p. 3636-3638 or V. Farina, V. Krishnamurthy, W. J. Scott, Org. React. 1997, 50, 1-652. Stannanes of the formula IV are either known or can be prepared by commonly known processes.

Suitable organometallic compounds IV are additionally organozinc compounds (compounds IV where Met=Zn-Hal where Hal=Cl, Br, especially Br). In that case, the reaction is effected under the conditions of a Negishi coupling, as known, for example, from A. Lützen, M. Hapke, Eur. J. Org. Chem., 2002, 2292-2297. Arylzinc compounds of the formula IV or alkylzinc compounds of the formula IV are either known or can be prepared by commonly known processes.

The reaction of IIIa and IIIb with the organometallic compound IV, especially in the case of the Suzuki coupling, is effected under basic conditions. Suitable bases are alkali metal carbonates and alkali metal hydrogencarbonates such as sodium carbonate, potassium carbonate, cesium carbonate, sodium hydrogencarbonate, alkaline earth metal carbonates and alkaline earth metal hydrogencarbonates such as magnesium carbonate or magnesium hydrogencarbonate, or tertiary amines such as triethylamine, trimethylamine, triisopropylamine or N-ethyl-N-diisopropylamine.

Typically, the coupling of the compounds IIIa and IIIb with the compound IV is effected in a solvent. Suitable solvents are organic solvents such as aromatics, e.g. toluene, mesitylene, acyclic ethers, e.g. 1,2-dimethoxyethane, cyclic ethers such as tetrahydrofuran or 1,4-dioxane, polyalkylene glycols such as diethylene glycol, carbonitriles such as acetonitrile, propionitrile, carboxamides such as dimethylformamide or dimethylacetamide. In the Suzuki coupling, the aforementioned solvents can also be used in a mixture with water; for example, the ratio of organic solvent to water may be in the range from 5:1 to 1:5.

At least one mole of the organometallic compound IV is used per mole of halogen atom to be exchanged. It may be advantageous to use a 5 to 30% molar excess of organometallic compound of the formula IV per mole of halogen atom to be exchanged.

If Z is different than Z*, a further coupling with an organometallic compound of the formula V is subsequently conducted. In terms of the process, the procedure is as in the reaction of the compound of the formulae IIIa and IIIb with the organometallic compound IV.

Step c)

The halogenation of compounds of the formulae VIa and VIb is typically effected with a brominating agent or a chlorinating agent. Suitable brominating agents or chlorinating agents are those mentioned in step a). In general, the molar ratio of brominating agent to compound of the formulation VIa and VIb to be halogenated is 10:1 to 30:1, preferably 15:1 to 25:1.

Step c) of the process according to the invention is typically undertaken in the presence of a solvent at elevated temperatures. Suitable solvents are aprotic solvents such as halogenated aromatics such as chlorobenzene or dichlorobenzenes or halogenated hydrocarbons. Also suitable are aqueous aprotic solvents.

It may be advantageous to conduct step c) in the presence of catalytic amounts of iodine.

The reaction temperature in step c) is typically 50° C. up to the boiling temperature of the solvent, in particular 80 to 150° C.

Step d)

Suitable process conditions for cyano-dehalogenation are described in J. March, Advanced Organic Chemistry, 4th edition, John Wiley & Sons Publishers (1992), p. 660-661, and in WO 2004/029028. One example of these is reaction with copper cyanide. Additionally suitable are alkali metal cyanides such as potassium cyanide and sodium cyanide, and also zinc cyanide. Typically, the cyanide source is used in excess. The reaction is generally effected in polar aprotic solvents in the presence of transition metals such as Pd(II) salts or Pd complexes, copper complexes or nickel complexes. The palladium catalyst can be prepared in situ from Pd(0) complexes such as tris(dibenzylideneacetone)dipalladium(0) and 1,1'-bis(diphenylphosphino)ferrocene. Preferred polar aprotic solvents are dimethylformamide, N-methylpyrrolidone, $(CH_3)_2SO$, dimethyl sulfone and sulfolane. The reaction is performed typically at temperatures of 80 to 160° C., preferably 100 to 140° C., especially preferably 130 to 150° C. The molar ratio of halogen atom to be exchanged to zinc cyanide is typically 1:1 to 1:3, preferably 1.5:2.5. Alternatively, it is also possible to use copper cyanide in N-methylpyrrolidone or sulfolane in the absence of a catalyst.

Step e)

Optionally, the reaction mixture obtained in step d), comprising at least one perylene compound of the formula I-A or mixtures thereof, is subjected to a partial or complete separation and/or a purifying step. The separation and/or purification in step e) can be effected by customary processes known to those skilled in the art, such as extraction, distillation, recrystallization, separation on suitable stationary phases, and a combination of these measures.

It may be advantageous to undertake a partial or full separation of the isomers obtained after reaction step a) and/or b) and/or c).

In a first specific embodiment of this subject, preference is given to a composition in which, in the compound of the formula I-A,
one of the Z substituents is cyano and the other Z substituent is unsubstituted phenyl;
one of the Z* substituents is cyano and the other Z* substituent is unsubstituted phenyl;
$R^1$, $R^4$, $R^5$ and $R^8$ are each hydrogen;
two of the $R^2$, $R^3$, $R^6$ and $R^7$ substituents are cyano and the other $R^2$, $R^3$, $R^6$ and $R^7$ substituents are hydrogen.

In a second specific embodiment of this subject, preference is given to a composition in which, in the compound of the formula I-A,
one of the Z substituents is cyano and the other Z substituent is phenyl bearing 1, 2 or 3 $C_1$-$C_4$-alkyl groups;
one of the Z* substituents is cyano and the other Z* substituent is phenyl bearing 1, 2 or 3 $C_1$-$C_4$-alkyl groups;
$R^1$, $R^4$, $R^5$ and $R^8$ are each hydrogen;
two of the $R^2$, $R^3$, $R^6$ and $R^7$ substituents are cyano and the other $R^2$, $R^3$, $R^6$ and $R^7$ substituents are hydrogen.

In a third specific embodiment of this subject, preference is given to a composition in which, in the compound of the formula I-A,
one of the Z substituents is cyano and the other Z substituent is $C_1$-$C_6$-alkyl;
one of the Z* substituents is cyano and the other Z* substituent is $C_1$-$C_6$-alkyl;
$R^1$, $R^4$, $R^5$ and $R^8$ are each hydrogen;
two of the $R^2$, $R^3$, $R^6$ and $R^7$ substituents are cyano and the other $R^2$, $R^3$, $R^6$ and $R^7$ substituents are hydrogen.

The present invention further provides a composition comprising at least one cyanated perylene compound of the formula I corresponding to the formula I-B

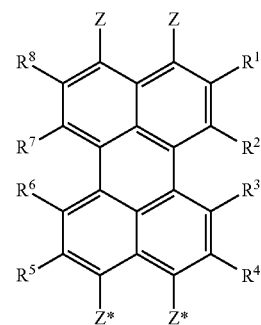

(I-B)

in which
one of the Z substituents is cyano and the other Z substituent is $COOR^9$;
one of the Z* substituents is cyano and the other Z* substituent is $COOR^9$;
$R^1$, $R^4$, $R^5$ and $R^8$ are hydrogen;

one of the $R^2$, $R^3$, $R^6$ or $R^7$ substituents is cyano and the other $R^2$, $R^3$, $R^6$ and $R^7$ substituents are hydrogen;

$R^9$ is hydrogen, $C_1$-$C_{10}$-alkyl, $C_2$-$C_{10}$-alkenyl, $C_2$-$C_{10}$-alkynyl, $C_3$-$C_{12}$-cycloalkyl or $C_6$-$C_{14}$-aryl, where $C_1$-$C_{10}$-alkyl, $C_2$-$C_{10}$-alkenyl, $C_2$-$C_{10}$-alkynyl are unsubstituted or bear one or more identical or different $R^a$ substituents, $C_3$-$C_{12}$-cycloalkyl is unsubstituted or bears one or more identical or different $R^b$ substituents and $C_6$-$C_{14}$-aryl is unsubstituted or bears one or more identical or different $R^{Ar}$ substituents, where $R^a$, $R^b$ and $R^{Ar}$ are each as defined above, or mixtures thereof, obtainable by a process in which f) a mixture of perylene compounds of the formulae VIIIa and VIIIb

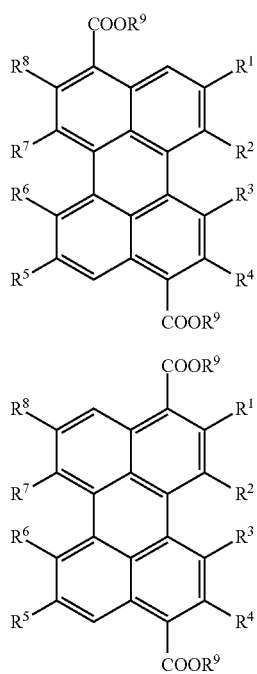

(VIIIa)

(VIIIb)

in which $R^1$, $R^2$, $R^3$, $R^4$, $R^5$, $R^6$, $R^7$ and $R^8$ are hydrogen; and $R^9$ is as defined above is halogenated to obtain a reaction mixture comprising compounds of the formulae IXa and IXb,

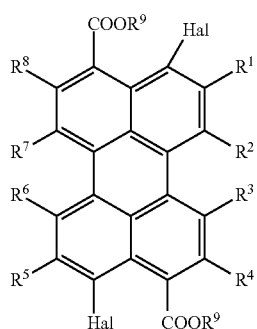

(IXa)

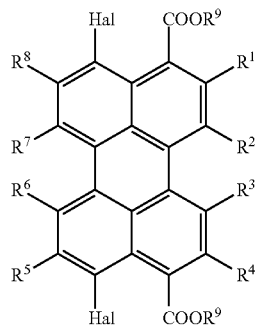

(IXb)

in which $R^1$, $R^2$, $R^3$, $R^4$, $R^5$, $R^6$, $R^7$ and $R^8$ are hydrogen or halogen selected from chlorine and bromine, where the $R^1$, $R^2$, $R^3$, $R^4$, $R^5$, $R^6$, $R^7$ and $R^8$ substituents which are not hydrogen are either all chlorine or all bromine;

Hal is halogen selected from chlorine and bromine, where the Hal substituents are either all chlorine or all bromine; and R is as defined above;

or mixtures thereof;

g) the compounds of the formulae IXa and IXb present in the reaction mixture obtained in step f) are subjected to a substitution of halogen for cyano groups, and optionally partly for hydrogen, to obtain at least one compound of the formula I-B or mixtures thereof; and h) the at least one compound of the formula I-B or mixtures thereof present in the reaction mixture obtained in step g) is optionally subjected to at least one separation and/or purification step.

Step f)

In terms of the process, step f) is conducted like step c).

Step g)

In terms of the process, step g) is conducted like step d).

In a specific embodiment of this subject, preference is given to a composition in which, in the compound of the formula I-B, one of the Z substituents is cyano and the other Z substituent is $C_1$-$C_6$-alkoxycarbonyl;

one of the Z* substituents is cyano and the other Z* substituent is $C_1$-$C_6$-alkoxycarbonyl;

$R^1$, $R^4$, $R^5$ and $R^8$ are each hydrogen;

one of the $R^2$, $R^3$, $R^6$ or $R^7$ substituents is cyano and the other $R^2$, $R^3$, $R^6$ or $R^7$ substituents are each hydrogen.

The inventive compound of the formula I and mixtures thereof or compositions comprising at least one cyanated perylene compound of the formula I and mixtures thereof as defined above are suitable as a fluorescent dye in color converters, for optical labels, for invisible marking of products, as fluorescent dyes, preferably as fluorescent labels for biomolecules, as pigments, as a fluorescent dye in a display based on fluorescence conversion; in a light-collecting plastics part optionally combined with a solar cell; as a pigment dye in electrophoretic displays; as a fluorescent dye in an application based on chemoluminescence.

The inventive compound of the formula I and mixtures thereof or compositions comprising at least one cyanated perylene compound of the formula I and mixtures thereof as defined above are particularly advantageously suitable as a fluorescent dye in a display based on fluorescence conversion. Displays of this kind generally comprise a transparent substrate, a fluorescent dye present on the substrate and a radiation source. Standard radiation sources emit blue (color-by-blue) or UV light (color-by-uv). The dyes absorb either the blue light or the UV light and are used as green emitters. In these displays, for example, red light is generated by excitation of the red emitter by a green emitter which absorbs blue or UV light. Suitable color-by-blue displays are described, for example, in WO 98/28946. Suitable color-by-uv displays are described, for example, by W. A. Crossland, I. D. Sprigle and A. B. Davey in Photoluminescent LCDs (PL-LCD) using phosphors Cambridge University and Screen Technology Ltd., Cambridge, UK.

The inventive compound of the formula I and mixtures thereof or compositions comprising at least one cyanated perylene compound of the formula I and mixtures thereof as defined above are also particularly suitable as fluorescence emitters in OLEDs in which they are excited either by electroluminescence or by a corresponding phosphorescence emitter via Förster energy transfer (FRET).

The inventive compound of the formula I and mixtures thereof or compositions comprising at least one cyanated perylene compound of the formula I and mixtures thereof as defined above are also particularly suitable in chemoluminescence applications. These include "glow sticks". They can be produced by dissolving at least one compound of the formula (I), for example, in an alkyl phthalate.

Chemoluminescence can be induced by mixing an oxalic ester with hydrogen peroxide, for example after these initially separate components are mixed by breaking a glass tube. The resulting reaction energy leads to excitation and fluorescence of the dyes. Glow sticks of this kind can be used as an emergency light, for example when angling, in marine emergency rescue vests or in other safety applications.

The inventive compound of the formula I and mixtures thereof or compositions comprising at least one cyanated perylene compound of the formula I and mixtures thereof as defined above are particularly suitable as a fluorescent dye in color converters for solar cells.

The present invention further provides color converters comprising at least one polymer as matrix material and at least one cyanated perylene compound of the formula I or mixtures thereof as defined above or compositions comprising at least one cyanated perylene compound of the formula I and mixtures thereof as defined above as a fluorescent dye.

The present invention further provides color converters comprising (I) at least one polymer as matrix material and (ii) at least one inventive cyanated perylene compound of the formula I or mixtures thereof or compositions comprising at least one cyanated perylene compound of the formula I and mixtures thereof as defined above as a fluorescent dye.

Component (i)

Suitable polymers are in principle all polymers capable of dissolving or homogeneously distributing the at least one cyanated perylene compound of the formula I or mixtures thereof in a sufficient amount.

Suitable polymers may be inorganic polymers or organic polymers.

Suitable inorganic polymers are, for example, silicates or silicon dioxide. A prerequisite for the use of inorganic polymers is that the at least one cyanated perylene compound of the formula I or mixtures thereof can be dissolved or homogeneously distributed therein without decomposition. In the case of silicates or silicon dioxide, for example, this can be accomplished by deposition of the polymer from a waterglass solution.

In a preferred embodiment, the organic polymers consist essentially of polystyrene, polycarbonate, polymethylmethacrylate, polyvinylpyrrolidone, polymethacrylate, polyvinyl acetate, polyvinyl chloride, polybutene, polyethylene glycol, silicone, polyacrylate, epoxy resin, polyvinyl alcohol, ethylene vinyl alcohol copolymer (EVOH), polyacrylonitrile, polyvinylidene chloride (PVDC), polystyreneacrylonitrile (SAN), polybutylene terephthalate (PBT), polyethylene terephthalate (PET), polyvinyl butyrate (PVB), polyvinyl chloride (PVC), polyamides, polyoxymethylenes, polyimides, polyetherimide or mixtures thereof.

Preferably, the at least one polymer consists essentially of polystyrene (PS), polycarbonate (PC), polymethylmethacrylate (PMMA), polyethylene terephthalate (PET) or mixtures thereof.

Most preferably, the at least one polymer consists essentially of polyethylene terephthalate, polystyrene or polycarbonate.

Polyethylene terephthalate is obtainable by condensation of ethylene glycol with terephthalic acid.

Polystyrene is understood here to mean, inter alia, all homo- or copolymers which result from polymerization of styrene and/or derivatives of styrene. Derivatives of styrene are, for example, alkylstyrenes such as alpha-methylstyrene, ortho-, meta-, para-methylstyrene, para-butylstyrene, especially para-tert-butylstyrene, alkoxystyrene such as para-methoxystyrene, para-butoxystyrene, para-tert-butoxystyrene.

In general, suitable polystyrenes have a mean molar mass $M_n$ of 10 000 to 1 000 000 g/mol (determined by GPC), preferably 20 000 to 750 000 g/mol, more preferably 30 000 to 500 000 g/mol.

In a preferred embodiment, the matrix of the color converter consists essentially or completely of a homopolymer of styrene or styrene derivatives.

In further preferred embodiments of the invention, the matrix consists essentially or completely of a styrene copolymer, which are likewise regarded as polystyrene in the context of this application. Styrene copolymers may comprise, as further constituents, for example, butadiene, acrylonitrile, maleic anhydride, vinylcarbazole or esters of acrylic, methacrylic or itaconic acid as monomers. Suitable styrene copolymers generally comprise at least 20% by weight of styrene, preferably at least 40% and more preferably at least 60% by weight of styrene. In another embodiment, they comprise at least 90% by weight of styrene.

Preferred styrene copolymers are styrene-acrylonitrile copolymers (SAN) and acrylo-nitrile-butadiene-styrene copolymers (ABS), styrene-1,1'-diphenylethene copolymers, acrylic ester-styrene-acrylonitrile copolymers (ASA), methyl methacrylate-acrylonitrile-butadiene-styrene copolymers (MABS).

A further preferred polymer is alpha-methylstyrene-acrylonitrile copolymer (AMSAN).

The styrene homo- or copolymers can be prepared, for example, by free-radical polymerization, cationic polymerization, anionic polymerization or under the influence of organometallic catalysts (for example Ziegler-Natta catalysis). This can lead to isotactic, syndiotactic or atactic polystyrene or copolymers. They are preferably prepared by free-radical polymerization. The polymerization can be performed as a suspension polymerization, emulsion polymerization, solution polymerization or bulk polymerization.

The preparation of suitable polystyrenes is described, for example, in Oscar Nuyken, Polystyrenes and Other Aromatic Polyvinyl Compounds, in Kricheldorf, Nuyken, Swift, New York 2005, p. 73-150 and references cited therein; and in Elias, Macromolecules, Weinheim 2007, p. 269-275.

Polycarbonates are polyesters of carbonic acid with aromatic or aliphatic dihydroxyl compounds. Preferred dihydroxyl compounds are, for example, methylenediphenylenedihydroxyl compounds, for example bisphenol A.

One means of preparing polycarbonates is the reaction of suitable dihydroxyl compounds with phosgene in an interfacial polymerization. Another means is the reaction with diesters of carbonic acid such as diphenyl carbonate in a condensation polymerization.

The preparation of suitable polycarbonates is described, for example, in Elias, Macromolecules, Weinheim 2007, p. 343-347.

In a preferred embodiment, polymers which have been polymerized with exclusion of oxygen are used. Preferably, the monomers during the polymerization comprised a total of not more than 1000 ppm of oxygen, more preferably not more than 100 ppm and especially preferably not more than 10 ppm.

Suitable polymers may comprise, as further constituents, additives such as flame retardants, antioxidants, light stabilizers, UV absorbers, free-radical scavengers, antistats. Stabilizers of this kind are known to those skilled in the art.

Suitable antioxidants or free-radical scavengers are, for example, phenols, especially sterically hindered phenols such as butylhydroxyanisole (BHA) or butylhydroxytoluene (BHT), or sterically hindered amines (HALS). Stabilizers of this kind are sold, for example, by BASF under the Irganox® trade name. In some cases, antioxidants and free-radical scavengers can be supplemented by secondary stabilizers such as phosphites or phosphonites, as sold, for example, by BASF under the Irgafos® trade name.

Suitable UV absorbers are, for example, benzotriazoles such as 2-(2-hydroxyphenyl)-2H-benzotriazole (BTZ), triazines such as (2-hydroxyphenyl)-s-triazine (HPT), hydroxybenzophenones (BP) or oxalanilides. UV absorbers of this kind are sold, for example, by BASF under the Uvinul® trade name.

In a preferred embodiment, TiO$_2$ is used as the sole UV absorber.

In a preferred embodiment of the invention, suitable polymers do not comprise any antioxidants or free-radical scavengers.

In a further embodiment of the invention, suitable polymers are transparent polymers.

In another embodiment, suitable polymers are opaque polymers.

The polymers mentioned serve as matrix material for suitable organic fluorescent dyes.

Component (ii)

Component (ii) comprises at least one cyanated perylene compound of the formula I or mixtures thereof or a composition comprising at least one cyanated perylene compound of the formula I or mixtures thereof. Especially preferably, the cyanated perylene compound of the formula I is selected from compounds of the formulae (1), (2), (3), (4), (5), (6), (7), (8), (9), (10), (11), (12), (13), (14), (15), (16), (17), (18), (19), (20)

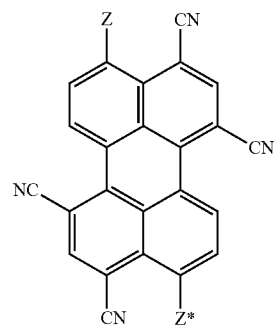

(1)

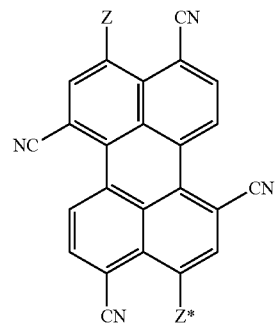

(2)

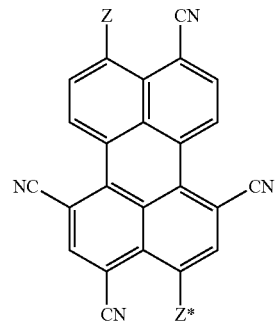

(3)

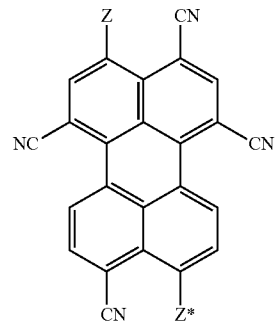

(4)

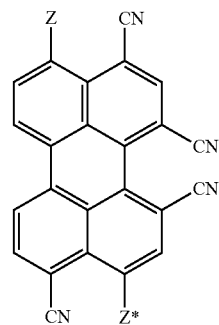

(5)

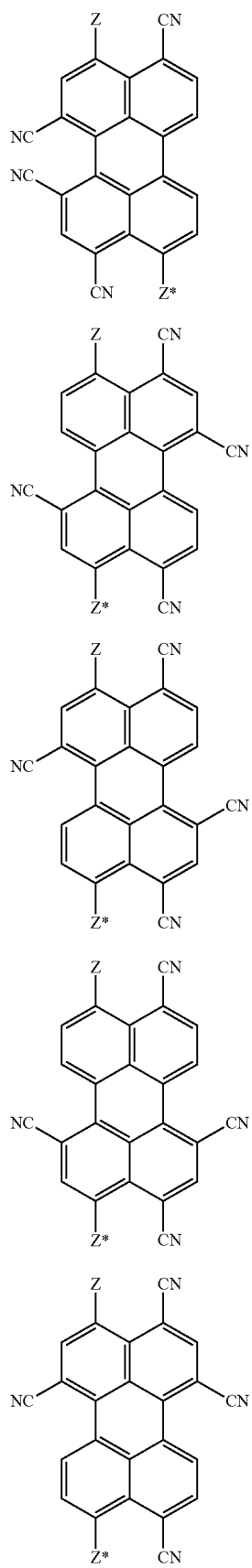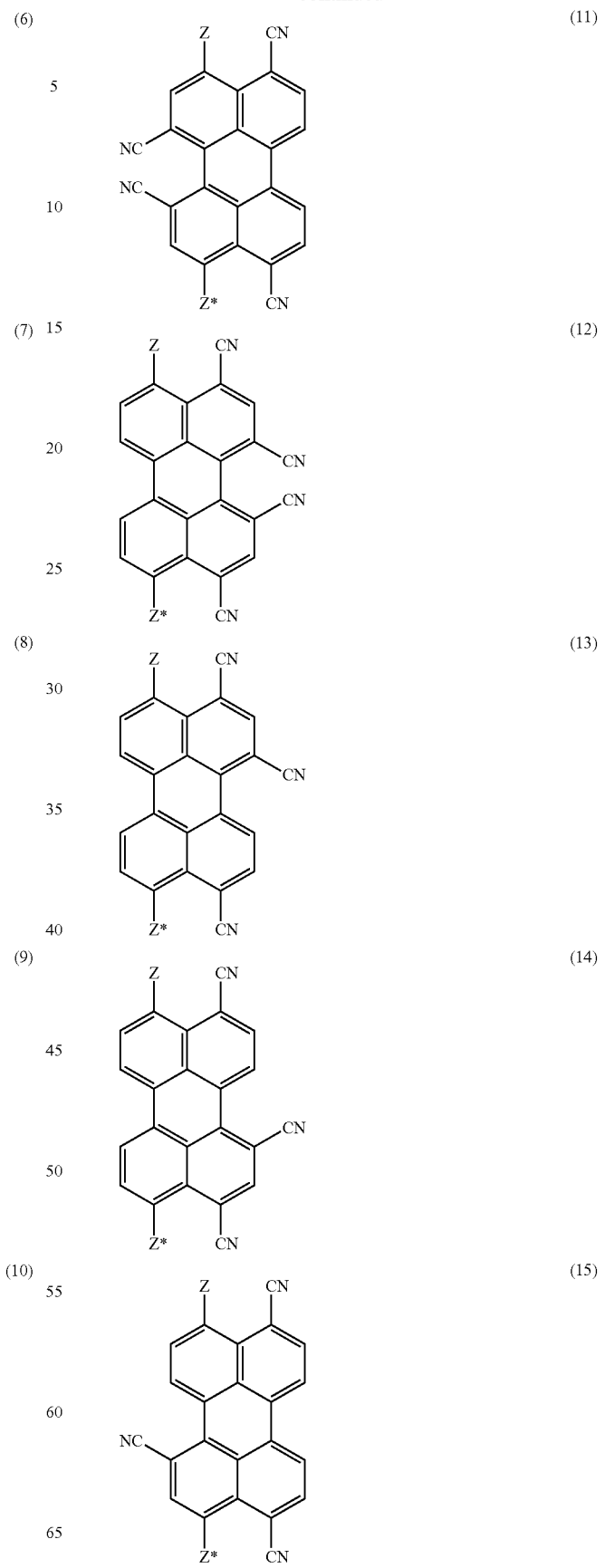

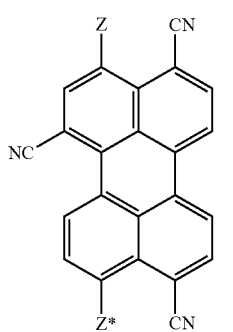

(16)

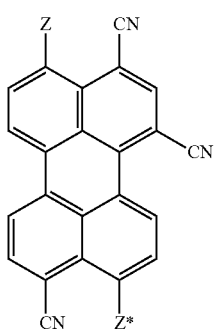

(17)

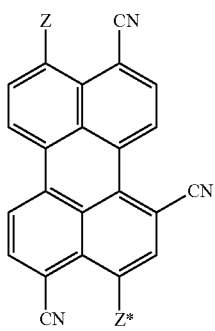

(18)

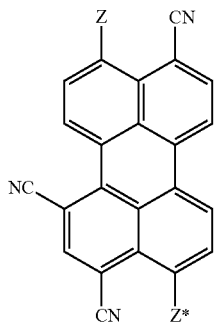

(19)

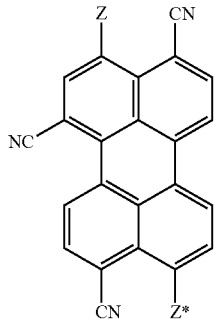

(20)

in which

Z is selected from $C_1$-$C_6$-alkyl, $C_1$-$C_6$-alkoxycarbonyl, phenyl, and phenyl bearing 1, 2 or 3 $C_1$-$C_4$-alkyl groups; and Z* is selected from $C_1$-$C_6$-alkyl, $C_1$-$C_6$-alkoxycarbonyl, phenyl, and phenyl bearing 1, 2 or 3 $C_1$-$C_4$-alkyl groups.

Specifically preferred among these are cyanated perylene compounds of the formulae (1) to (20) in which Z and Z* each have the same definition.

Specific preference is given to cyanated perylene compounds of the formulae (1), (2), (3), (4), (5), (6), (7), (8), (9), (10), (11), (12) and mixtures thereof in which Z and Z* are each isopropyl.

Specific preference is likewise given to cyanated perylene compounds of the formulae (1), (2), (3), (4), (5), (6), (7), (8), (9), (10), (11), (12) and mixtures thereof in which Z and Z* are each phenyl.

Specific preference is likewise given to cyanated perylene compounds of the formulae (1), (2), (3), (4), (5), (6), (7), (8), (9), (10), (11), (12) and mixtures thereof in which Z and Z* are each 2-methylphenyl.

Specific preference is likewise given to cyanated perylene compounds of the formulae (1), (2), (3), (4), (5), (6), (7), (8), (9), (10), (11), (12) and mixtures thereof in which Z and Z* are each 2,6-dimethylphenyl.

Specific preference is likewise given to cyanated perylene compounds of the formulae (13), (14), (15), (16), (17), (18), (19), (20) and mixtures thereof in which Z and Z* are each isobutylcarboxy.

The cyanated perylene compound of the formula I or mixtures thereof or the composition comprising at least one cyanated perylene compound of the formula I and mixtures thereof may either be dissolved in the polymer or be in the form of a mixture in homogeneous distribution. Preferably, the perylene compound of the formula I or mixtures thereof is dissolved in the polymer. Likewise preferably, the composition comprising at least one cyanated perylene compound of the formula I or mixtures thereof is dissolved in the polymer.

In a preferred embodiment, inventive color converters comprise further fluorescent colorants. Suitable further fluorescent colorants are, for example, red-fluorescing fluorescent colorants. In many cases, fluorescent colorants are combined with one another such that color converters which can convert blue light to white light with good color rendering are obtained.

Suitable further fluorescent colorants are, for example, inorganic fluorescent colorants. Particularly preferred among these are those from the class of the rare earth-doped aluminates, silicates, nitrides and garnets. Further inorganic lighting colorants are, for example, those mentioned in "Luminescence—from Theory to Applications", Cees Ronda [ed.], Wiley-VCH, 2008, Chapter 7, "Luminescent Materials for Phosphor-Converted LEDs", Th. Jüstel, pages 179-190.

Garnets are compounds of the general formula $X_3Y_2[ZO_4]_3$ in which Z is a divalent cation such as Ca, Mg, Fe, Mn, Y is a trivalent cation such as Al, Fe, Cr, rare earths, and Z is Si, Al, $Fe^{3+}$, $Ga^{3+}$. The garnet is preferably yttrium aluminum garnet $Y_3Al_5O_{12}$ doped with $Ce^{3+}$, $Gd^{3+}$, $Sm^{3+}$, $Eu^{2+}$, $Eu^{3+}$, $Dy^{3+}$, $Tb^{3+}$ or mixtures thereof.

Suitable nitrides are described, for example, in U.S. Pat. No. 8,274,215, which is hereby fully incorporated by reference. Suitable silicates are described, for example, in U.S. Pat. No. 7,906,041 and U.S. Pat. No. 7,311,858, which is hereby fully incorporated by reference.

Suitable aluminates are described, for example, in U.S. Pat. No. 7,755,276, which is hereby fully incorporated by reference.

Suitable aluminate phosphors of the formula $SrLu_{2-x}Al_4O_{12}:Ce_x$ in which x is a value from the range from 0.01 to 0.15 are known from WO2012010244. Luminophores of the composition $MLn_2QR_4O_{12}$ where M is at least one of the elements Mg, Ca, Sr or Ba; Ln is at least one of the elements Sc, Y, La, Ce, Pr, Nd, Sm, Eu, Gd, Tb, Dy, Ho, Er, Tm, Yb and Lu; Q is one of the elements Si, Ge, Sn, and Pb, and R, finally, is at least one of the elements B, Al, Ga, In and Tl, are known from US 2004/0062699.

In addition, all organic red or pink fluorescent dyes are particularly suitable. In a further embodiment, further fluorescent colorants comprise further orange- or yellow-fluorescing fluorescent dyes. Suitable organic fluorescent red dyes have, for example, the general formula X

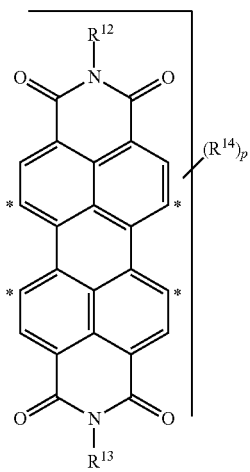

(X)

where p is 1 to 4, $R^{12}$, $R^{13}$ are each independently $C_1$-$C_{30}$-alkyl, $C_3$-$C_8$-cycloalkyl, $C_6$-$C_{14}$-aryl, hetaryl, $C_6$-$C_{14}$-aryl-$C_1$-$C_{10}$-alkylene, where the aromatic ring in the three latter radicals is unsubstituted or mono- or polysubstituted by $C_1$-$C_{10}$-alkyl, and $R^{14}$ is $C_1$-$C_{30}$-alkoxy or $C_6$-$C_{14}$-aryloxy which is unsubstituted or mono- or polysubstituted by $C_1$-$C_{10}$-alkyl, where the $R^{14}$ radicals are at one or more of the positions indicated by *.

Preferably, $R^{12}$ and $R^{13}$ are each independently selected from $C_1$-$C_{10}$-alkyl, 2,6-di($C_1$-$C_{10}$-alkyl)aryl and 2,4-di($C_1$-$C_{10}$-alkyl)aryl. More preferably, $R^{12}$ and $R^{13}$ are identical. Very particularly, $R^{12}$ and $R^{13}$ are each 2,6-diisopropylphenyl or 2,4-di-tert-butylphenyl. $R^{14}$ is preferably phenoxy or $C_1$-$C_{10}$-alkylphenoxy, more preferably 2,6-dialkylphenoxy, 2,4-dialkylphenoxy. Especially preferably, $R^{14}$ is phenoxy, 2,6-diisopropylphenoxy, 2,4-di-tert-butylphenoxy or 4-tert-octylphenoxy.

More particularly, suitable further organic fluorescent dyes are selected from the compounds of the formulae X-1, X-2 and X-3

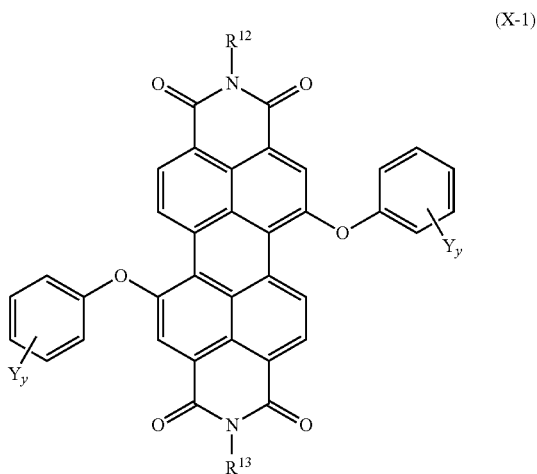

(X-1)

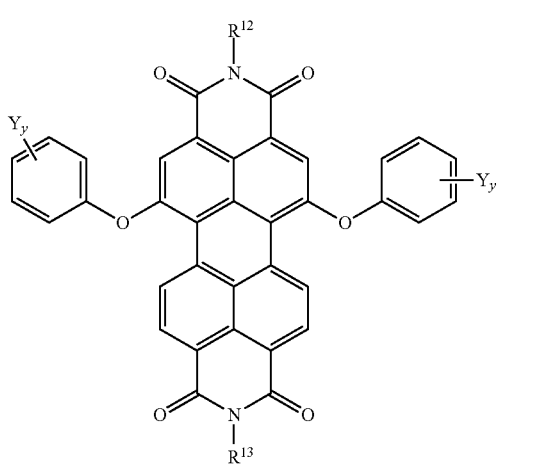

(X-2)

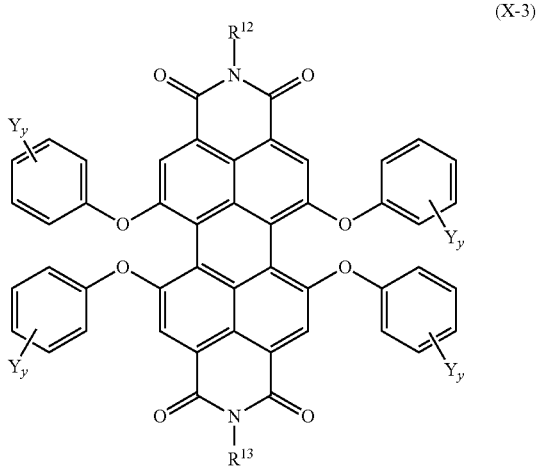

(X-3)

in which $R^{12}$ and $R^{13}$ are each as defined above and especially as defined above with preference, Y is linear or branched $C_1$-$C_{10}$-alkyl; and y is 0, 1, 2, or 3.

Further examples of particularly suitable further organic fluorescent dyes are the perylene derivatives specified in WO2007/006717 at page 1 line 5 to page 22 line 6.

Particularly suitable further organic fluorescent dyes are: N,N'-bis(2,6-diisopropylphenyl)-1,6,7,12-tetraphenoxyperylene-3,4;9,10-tetracarboximide, N,N'-bis(2,6-diisopropylphenyl)-1,7-di(2,6-diisopropylphenoxy)perylene-3,4;9,10-tetracarboximide, N,N'-bis(2,6-diisopropylphenyl)-1,6-di(2,6-diisopropyl-phenoxy)perylene-3,4;9,10-tetracarboximide, N,N'-bis(2,6-diisopropylphenyl)-1,7-di(p-tert-octylphenoxy)perylene-3,4;9,10-tetracarboximide, N,N'-bis(2,6-diisopropylphenyl)-1,6-di(p-tert-octylphenoxy)perylene-3,4;9,10-tetracarboximide, N,N'-bis(2,6-diisopropylphenyl)-1,7-diphenoxyperylene-3,4;9,10-tetracarboximide, N,N'-bis(2,6-diisopropylphenyl)-1,6-diphenoxyperylene-3,4;9,10-tetracarboximide. Preferably, the further organic fluorescent dye is selected from N,N'-bis(2,6-diisopropylphenyl)-1,7-di(2,6-diisopropylphenoxy)perylene-3,4;9,10-tetracarboximide, N,N'-bis(2,6-diisopropylphenyl)-1,6-di(2,6-diisopropylphenoxy)perylene-3,4;9, 10-tetracarboximide and mixtures thereof.

In a further embodiment, inventive color converters additionally comprise at least one further organic fluorescent dye of the formulae XI and XII

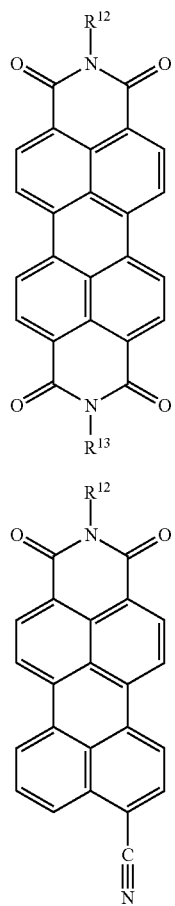

where $R^{12}$ and $R^{13}$ are each as defined above.

In one embodiment of the invention, inventive color converters have a laminate structure. They may either have a monolayer structure or a multilayer structure, generally composed of a plurality of polymer layers comprising one or more fluorescent colorants and/or scattering bodies.

In one embodiment, the color converters consist of a plurality of polymer layers which have been laminated together to form a composite and wherein the various fluorescent colorants and/or scattering bodies may be present in different polymer layers.

If inventive color converters comprise more than one fluorescent colorant, it is possible in one embodiment of the invention for a plurality of fluorescent colorants to be present alongside one another in one layer.

In another embodiment, the various fluorescent colorants are present in various layers.

In a preferred embodiment, inventive color converters additionally comprise at least one further organic fluorescent dye of formula (X), scattering bodies based on $TiO_2$ and at least one polymer consisting essentially of polystyrene, polyethylene terephthalate (PET) or polycarbonate.

In a further preferred embodiment, inventive color converters additionally comprise at least one further organic fluorescent dye of formula (X) and at least one further organic fluorescent dye of formula (XI) or (XII), scattering bodies based on $TiO_2$ and at least one polymer consisting essentially of polystyrene, polyethylene terephthalate or polycarbonate.

In a particularly preferred embodiment, inventive color converters comprise at least one compound of the formula I or mixtures thereof or a composition comprising at least one compound of the formula I or mixtures thereof, a further red organic fluorescent dye selected from N,N'-bis(2,6-diisopropylphenyl)-1,6,7,12-tetraphenoxyperylene-3,4;9,10-tetracarboximide, N,N'-bis(2,6-diisopropylphenyl)-1,7-di(2,6-diisopropylphenoxy) perylene-3,4;9,10-tetracarboximide, N,N'-bis(2,6-diisopropylphenyl)-1,6-di(2,6-diiso-propylphenoxy)perylene-3,4;9,10-tetracarboximide, and at least one further organic fluorescent dye selected from N,N'-bis(2,6-diisopropylphenyl)perylene-3,4;9,10-tetracarboximide or N'-(2,6-diisopropylphenyl)-perylene-9-cyano-3,4-dicarboximide, a scattering body based on $TiO_2$ and at least one polymer consisting essentially of polystyrene, polyethylene terephthalate or polycarbonate.

Typically, the concentration of inventive organic fluorescent dye of the formula I or mixtures thereof is 0.001 to 0.5% by weight, preferably 0.005 to 0.2% by weight, most preferably 0.01 to 0.1% by weight, based in each case on the amount of polymer used. Typically, the concentration of the red organic fluorescent dye is 0.0001 to 0.5% by weight, preferably 0.002 to 0.1% by weight, most preferably 0.005 to 0.05% by weight, based on the amount of the polymer used.

The ratio of at least one inventive organic fluorescent dye of the formula I or mixtures thereof to at least one further red organic fluorescent dye is typically in the range from 4:1 to 15:1, preferably 6:1 to 12:1.

In a very particularly preferred embodiment, inventive color converters comprise
  at least one inventive compound of the formula I, preferably selected from compounds of the formulae (1), (2), (3), (4), (5), (6), (7), (8), (9), (10), (11), (12) and mixtures thereof, or a composition comprising at least one cyanated perylene compound of the formula I, preferably selected from compounds of the formulae (1), (2), (3), (4), (5), (6), (7), (8), (9), (10), (11), (12) and mixtures thereof, as organic fluorescent dye;
  additionally N,N'-bis(2,6-diisopropylphenyl)-1,7-di(2,6-diisopropylphenoxy)perylene-3,4;9,10-tetracarboximide and/or N,N'-bis(2,6-diisopropylphenyl)-1,6-di(2,6-diisopropylphenoxy)perylene-3,4;9,10-tetracarboximide as red organic fluorescent dye;
  scattering bodies based on $TiO_2$; and
  at least one polymer consisting essentially of polystyrene.

Among these, specific preference is given to perylene compounds of the formulae (1), (2), (3), (4), (5), (6), (7), (8), (9), (10), (11), (12) and mixtures thereof in which Z and Z* each have the same definition.

In a further very particularly preferred embodiment, inventive color converters comprise
- at least one inventive compound of the formula I, preferably selected from compounds of the formulae (13), (14), (15), (16), (17), (18), (19), (20) and mixtures thereof, or a composition comprising at least one cyanated perylene compound of the formula I, preferably selected from compounds of the formulae (13), (14), (15), (16), (17), (18), (19), (20) and mixtures thereof, as organic fluorescent dye;
- additionally N,N'-bis(2,6-diisopropylphenyl)-1,7-di(2,6-diisopropylphenoxy)perylene-3,4;9,10-tetracarboximide and/or N,N'-bis(2,6-diisopropylphenyl)-1,6-di(2,6-diisopropylphenoxy)perylene-3,4;9,10-tetracarboximide as red organic fluorescent dye;
- scattering bodies based on TiO$_2$; and
- at least one polymer consisting essentially of polystyrene.

Among these, specific preference is given to perylene compounds of the formulae (13), (14), (15), (16), (17), (18), (19), (20) and mixtures thereof in which Z and Z* each have the same definition.

In a further very particularly preferred embodiment, inventive color converters comprise
- at least one inventive compound of the formula I, preferably selected from compounds of the formulae (1), (2), (3), (4), (5), (6), (7), (8), (9), (10), (11), (12) and mixtures thereof, or a composition comprising at least one cyanated perylene compound of the formula I, preferably selected from compounds of the formulae (1), (2), (3), (4), (5), (6), (7), (8), (9), (10), (11), (12) and mixtures thereof, as organic fluorescent dye;
- additionally N,N'-bis(2,6-diisopropylphenyl)-1,7-di(2,6-diisopropylphenoxy)perylene-3,4;9,10-tetracarboximide and/or N,N'-bis(2,6-diisopropylphenyl)-1,6-di(2,6-diisopropylphenoxy)perylene-3,4;9,10-tetracarboximide as red organic fluorescent dye;
- scattering bodies based on TiO$_2$; and
- at least one polymer consisting essentially of PET.

Among these, specific preference is given to perylene compounds of the formulae (1), (2), (3), (4), (5), (6), (7), (8), (9), (10), (11), (12) and mixtures thereof in which Z and Z* each have the same definition.

In a further very particularly preferred embodiment, inventive color converters comprise
- at least one inventive compound of the formula I, preferably selected from compounds of the formulae (13), (14), (15), (16), (17), (18), (19), (20) and mixtures thereof, or a composition comprising at least one cyanated perylene compound of the formula I, preferably selected from compounds of the formulae (13), (14), (15), (16), (17), (18), (19), (20) and mixtures thereof, as organic fluorescent dye;
- additionally N,N'-bis(2,6-diisopropylphenyl)-1,7-di(2,6-diisopropylphenoxy)perylene-3,4;9,10-tetracarboximide and/or N,N'-bis(2,6-diisopropylphenyl)-1,6-di(2,6-diisopropylphenoxy)perylene-3,4;9,10-tetracarboximide as red organic fluorescent dye;
- scattering bodies based on TiO$_2$; and
- at least one polymer consisting essentially of PET.

Among these, specific preference is given to perylene compounds of the formulae (13), (14), (15), (16), (17), (18), (19), (20) and mixtures thereof in which Z and Z* each have the same definition.

In a further very particularly preferred embodiment, inventive color converters comprise
- at least one inventive compound of the formula I, preferably selected from compounds of the formulae (1), (2), (3), (4), (5), (6), (7), (8), (9), (10), (11), (12) and mixtures thereof, or a composition comprising at least one cyanated perylene compound of the formula I, preferably selected from compounds of the formulae (1), (2), (3), (4), (5), (6), (7), (8), (9), (10), (11), (12) and mixtures thereof, as organic fluorescent dye;
- additionally N,N'-bis(2,6-diisopropylphenyl)-1,7-di(2,6-diisopropylphenoxy)perylene-3,4;9, 10-tetracarboximide and/or N,N'-bis(2,6-diisopropylphenyl)-1,6-di(2,6-diisopropylphenoxy)perylene-3,4;9,10-tetracarboximide as red organic fluorescent dye;
- scattering bodies based on TiO$_2$; and
- at least one polymer consisting essentially of polycarbonate.

Among these, specific preference is given to perylene compounds of the formulae (1), (2), (3), (4), (5), (6), (7), (8), (9), (10), (11), (12) and mixtures thereof in which Z and Z* each have the same definition.

In a further very particularly preferred embodiment, inventive color converters comprise
- at least one inventive compound of the formula I, preferably selected from compounds of the formulae (13), (14), (15), (16), (17), (18), (19), (20) and mixtures thereof, or a composition comprising at least one cyanated perylene compound of the formula I, preferably selected from compounds of the formulae (13), (14), (15), (16), (17), (18), (19), (20) and mixtures thereof, as organic fluorescent dye;
- additionally N,N'-bis(2,6-diisopropylphenyl)-1,7-di(2,6-diisopropylphenoxy)perylene-3,4;9,10-tetracarboximide and/or N,N'-bis(2,6-diisopropylphenyl)-1,6-di(2,6-diisopropylphenoxy)perylene-3,4;9,10-tetracarboximide as red organic fluorescent dye;
- scattering bodies based on TiO$_2$; and
- at least one polymer consisting essentially of polycarbonate.

Among these, specific preference is given to perylene compounds of the formulae (13), (14), (15), (16), (17), (18), (19), (20) and mixtures thereof in which Z and Z* each have the same definition.

If the color converter has a multilayer structure, in one embodiment, one layer comprises at least one red fluorescent dye and another layer at least one inventive fluorescent dye of the formula I or mixtures thereof.

In one embodiment, the at least one red organic fluorescent dye is in the layer of the color converter facing the LED. In another embodiment, the at least one green or green/yellow fluorescent dye s in the layer of the color converter facing the LED.

In a further embodiment, a scattering body is present in the layer facing the LED, above that a color converter and above that in turn optionally a further layer containing a scattering body.

In a preferred embodiment, the color converter has a bilayer structure with a red-fluorescing layer and a green/yellow-fluorescing layer comprising at least one fluorescent dye present in accordance with the invention, with the red layer facing the blue light source. In this embodiment, both layers comprise TiO$_2$ as a scattering body.

A further preferred embodiment of color converters has a monolayer structure, with at least one fluorescent dye of the formula I present in accordance with the invention and mixtures thereof and at least one red fluorescent dye of formula (XII) and scattering bodies encompassed in one layer. The scattering body is preferably titanium dioxide. In this embodiment, the polymer preferably consists of polystyrene, PET or polycarbonate.

In one embodiment, at least one polymer layer of the color converter has been mechanically reinforced with glass fibers.

Inventive color converters may be in any desired geometric arrangement. The color converters may, for example, be in the form of films, sheets or plaques. Equally, the matrix comprising organic fluorescent colorants may be in droplet form or hemispherical form or in the form of lenses with convex and/or concave, flat or spherical surfaces.

"Casting" refers to the embodiment where LEDs or components comprising LEDs are cast or enveloped fully with a polymer comprising organic fluorescent dye.

In one embodiment of the invention, the polymer layers (matrices) comprising organic fluorescent dye are 25 to 200 micrometers thick, preferably 35 to 150 μm and particularly 50 to 100 μm.

In another embodiment, the polymer layers comprising organic fluorescent dye are 0.2 to 5 millimeters thick, preferably 0.3 to 3 mm and more preferably 0.4 to 1 mm.

If the color converters consist of one layer or they have a laminate structure, the individual layers, in a preferred embodiment, are continuous and do not have any holes or interruptions.

The concentration of the organic fluorescent dyes in the polymer is set as a function of the thickness of the color converter and the type of polymer. If a thin polymer layer is used, the concentration of the organic fluorescent dye is generally higher than in the case of a thick polymer layer.

In a preferred embodiment, at least one of the layers or matrices comprising fluorescent dye comprises scattering bodies for light.

In a further preferred embodiment of the multilayer structure, a plurality of layers comprising fluorescent dye and one or more layers comprising scattering bodies without fluorescent dye are present.

Suitable scattering bodies are inorganic white pigments, for example titanium dioxide, barium sulfate, lithopone, zinc oxide, zinc sulfide, calcium carbonate having a mean particle size to DIN 13320 of 0.01 to 10 μm, preferably 0.1 to 1 μm, more preferably 0.15 to 0.4 μm.

Scattering bodies are typically present in an amount of 0.01 to 4.0% by weight, preferably 0.05 to 2% by weight, more preferably 0.1 to 1% by weight, based in each case on the polymer in the layer comprising scattering bodies.

Inventive color converters may optionally comprise further constituents such as a backing layer.

Backing layers serve to impart mechanical stability to the color converter. The type of material for the backing layers is not crucial, provided that it is transparent and has the desired mechanical strength. Suitable materials for backing layers are, for example, glass or transparent rigid organic polymers such as polycarbonate, polystyrene or polymethacrylates or polymethylmethacrylates.

Backing layers generally have a thickness of 0.1 mm to 10 mm, preferably 0.3 mm to 5 mm, more preferably 0.5 mm to 2 mm.

In one embodiment of the invention, inventive color converters have at least one barrier layer against oxygen and/or water, as disclosed in WO 2012/152812. Examples of suitable barrier materials for barrier layers are, for example, glass, quartz, metal oxides, $SiO_2$, a multilayer system composed of alternating layers of $Al_2O_3$ and $SiO_2$ layers, titanium nitride, $SiO_2$/metal oxide multilayer materials, polyvinyl alcohol, polyacrylonitrile, polyvinylidene chloride (PVDC), liquid crystal polymers (LCP), polystyrene-acrylonitrile (SAN), polybutylene terephthalate (PBT), polybutylene naphthalate (PBN), polyethylene terephthalate (PET), polyethylene naphthalate (PEN), polyvinyl butyrate (PBT), polyvinyl chloride (PVC), polyamides, polyoxymethylenes, polyimides, polyetherimides, epoxy resins, polymers which derive from ethylene-vinyl acetate (EVA) and polymers which derive from ethylene-vinyl alcohol (EVOH).

A preferred material for barrier layers is glass or a multilayer system composed of alternating layers of $Al_2O_3$ and $SiO_2$ layers.

Preferably, suitable barrier layers have low permeability for oxygen.

More preferably, suitable barrier layers have low permeability for oxygen and water.

Inventive color converters are especially suitable for the conversion of blue light to green/yellow light.

More particularly, they are suitable for conversion of light emitted by blue LEDs. Suitable LEDs are, for example, those based on gallium nitride (GaN) or indium gallium nitride (InGaN). Likewise possible is use for conversion of light produced by mercury lamps, by organic light-emitting diodes (OLEDs) or by UV LEDs.

They are additionally suitable for applications as a light-collecting system (fluorescence collector) in photovoltaics and in fluorescence conversion solar cells.

In a further embodiment, the inventive color converters are used for the conversion of blue light.

In a further embodiment, the color converter is used for conversion of light which has been produced by a blue diode, using at least one compound of the formula I or mixtures thereof as a fluorescent dye rather than Ce:YAG as a radiation converter, or a composition comprising at least one compound of the formula I or mixtures thereof. Preferably, the color converter comprises, as fluorescent dye, in addition to the inventive compound of the formula I or mixtures thereof, a red organic fluorescent dye. The red organic fluorescent dye is preferably selected from the compounds of the formulae X, XI and XII. In this embodiment, the blue LED and the color converter are in a remote phosphor arrangement. The color rendering of such an LED meets high demands.

In a further embodiment, the color converter is used for conversion of light which has been produced by a blue diode, using at least one compound of the formula I or mixtures thereof or a composition comprising at least one compound of the formula I or mixtures thereof as a fluorescent dye in combination with at least one inorganic fluorescent colorant selected from rare earth-doped aluminates, silicates, nitrides and garnets, especially cerium-doped yttrium aluminum garnet. In this embodiment, the blue LED and the color converter are in a remote phosphor arrangement.

Inventive color converters on Irradiation with light, especially with blue LED light, exhibit a high quantum yield. In addition, they have a high photostability on illumination with blue light. Moreover, they are stable toward oxygen and water. They emit pleasant light with good color rendering. A further advantage is that color converters comprising no rare earths can be provided. Inventive color converters comprising cyanated compounds of the formula I or mixtures thereof or a composition comprising at least one compound of the formula I or mixtures thereof together with inorganic fluorescers doped with rare earths improve the color rendering value of a lighting device which has been produced with a blue LED and comprises Ce:YAG as converter material.

Inventive color converters can be produced by different processes.

In one embodiment, the process for producing inventive color converters comprises the dissolution of the at least one polymer and the at least one organic fluorescent dye in a solvent and subsequent removal of the solvent.

In another embodiment, the process for producing inventive color converters comprises the extrusion of the at least one organic fluorescent dye with the at least one polymer.

The invention further provides lighting devices comprising at least one LED and at least one inventive color converter. The at least one LED is preferably blue and emits light preferably within a wavelength range from 400 to 500 nm, preferably 420 to 480 nm, more preferably 440 to 470 nm, most preferably at 445 to 460 nm.

In one embodiment, inventive lighting devices comprise exactly one LED. In another embodiment, inventive lighting devices comprise two or more LEDs.

In one embodiment, inventive lighting devices comprise a plurality of LEDs, all of which are blue. In another embodiment, inventive lighting devices comprise a plurality of LEDs, at least one LED being blue and at least one LED not being blue but emitting light in another color, for example red.

Furthermore, the type of LED used is not crucial for the inventive lighting devices. In a preferred embodiment, the power density of the LED used is less than 20 mW/cm$^2$, preferably less than 15 mW/cm$^2$. The use of LEDs of higher power densities, such as or 30 mW/cm$^2$, is likewise possible. However, a higher power density of the LED can reduce the lifetime of the fluorescent dyes and the color converters.

Inventive color converters can be used in combination with LEDs in virtually any geometric form and irrespective of the construction of the lighting device.

In one embodiment, color converter and LED are in a phosphor on a chip arrangement.

Preferably, inventive color converters are used in a remote phosphor setup. In this case, the color converter is spatially separated from the LED. In general, the distance between LED and color converter is from 0.1 cm to 50 cm, preferably 0.2 to 10 cm and most preferably 0.5 to 2 cm. Between color converter and LED may be different media such as air, noble gases, nitrogen or other gases or mixtures thereof.

The color converter may, for example, be arranged concentrically around the LED or have a planar geometry. It may take the form, for example, of a plaque, sheet or film, be in droplet form or take the form of a casting.

Inventive lighting devices are suitable for lighting in interiors, outdoors, of offices, of vehicles, in torches, games consoles, streetlights, traffic signs.

Inventive lighting devices exhibit a high quantum yield. In addition, they have a long lifetime, especially a high photostability on illumination with blue light. They emit pleasant light with good color rendering.

EXAMPLES

Various fluorescent dyes were synthesized. The fluorescent dyes produced according to the examples were used to produce color converters. For this purpose, these were incorporated as described hereinafter into a matrix composed of a polymer. The polymer used was PMMA (Plexiglas® 6N from Evonik), polystyrene (PS168 N from BASF) and PC (Macrolon® 2808 from Bayer).

Production of the Color Converters for Testing of the Dyes:

About 2.5 g of polymer and 0.02% by weight of dye were dissolved in about 5 ml of methylene chloride, and 0.5% by weight of TiO$_2$ was dispersed therein, based in each case on the amount of polymer used. The solution/dispersion obtained was coated onto a glass surface using an applicator frame (wet film thickness 400 µm). After the solvent had dried off, the film was detached from the glass and dried in a vacuum drying cabinet at 50° C. overnight. Two circular film pieces having a diameter of 15 mm were punched out of each film of thickness 80 to 85 µm, and these served as analysis samples.

Fluorescence quantum yields (FQY) of the analysis samples were measured with the C9920-02 quantum yield measuring system (from Hamamatsu). This was done by illuminating each of the samples with light of 450 to 455 nm in an integration sphere (Ulbricht sphere). By comparison with the reference measurement in the Ulbricht sphere without sample, the unabsorbed fraction of the excitation light and the fluorescent light emitted by the sample are determined by means of a CCD spectrometer. Integration of the intensities over the spectrum of the unabsorbed excitation light or over that of the emitted fluorescent light gives the degree of absorption or fluorescence intensity or fluorescence quantum yield of each sample.

Example 1

Mixture of Compounds of the Formulae (1.a) and (1.b)

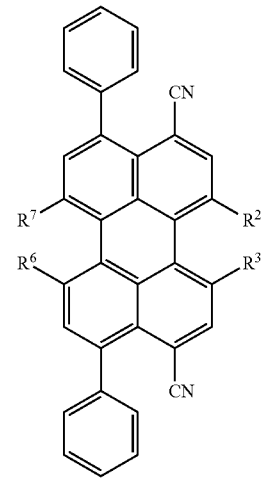

(1.a)

-continued

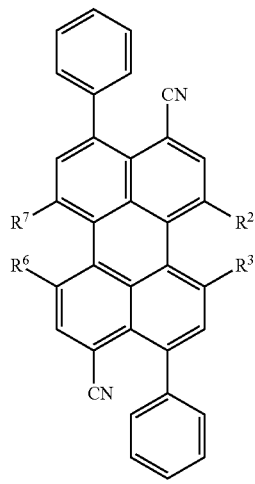

(1.b)

in which
two of the $R^2$, $R^3$, $R^6$ and $R^7$ substituents are hydrogen; and two of the $R^2$, $R^3$, $R^6$ and $R^7$ substituents are cyano.

1.1 3,9-Dibromoperylene and 3,10-dibromoperylene

A mixture of 14.9 g (59 mmol) of perylene, 400 ml of acetic acid and 18.9 g (236 mmol) of bromine was stirred at 40° C. for four hours. The excess bromine was subsequently destroyed by adding sodium thiosulfate solution. The precipitate was filtered off, washed with water and dried under reduced pressure. This gave 25.46 g (quant.) of the title compounds as a yellowish precipitate.

1.2 3,9-Diphenylperylene and 3,10-diphenylperylene

A mixture of 1.23 g (3 mmol) of 3,9-dibromoperylene and 3,10-dibromoperylene from example 1.1, 30 ml of toluene, 1.46 g (12 mmol) of phenylboronic acid, 2.49 g (18 mmol) of potassium carbonate, 8 ml of water, 0.24 g (0.2 mmol) of tetrakistriphenylphosphinepalladium was heated to 90° C. for 60 hours. After the reaction mixture had been cooled, it was diluted with toluene, the phases were separated and the toluene phase was purified by means of column filtration with silica gel. This gave 1.1 g (92%) of the title compound as a yellow solid. Rf (petroleum ether:toluene 5:1)=0.31.

1.3 Mixture of Compounds of the Formulae (1.3a) and (1.3b)

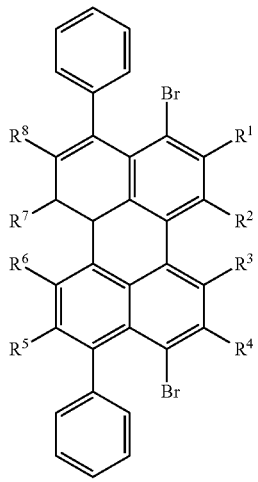

(1.3a)

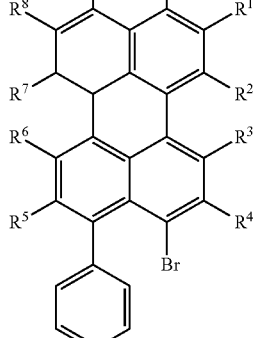

(1.3b)

in which
at least two of the $R^1$, $R^2$, $R^3$, $R^4$, $R^5$, $R^6$, $R^7$ and $R^8$ substituents are bromine, and the other $R^1$, $R^2$, $R^3$, $R^4$, $R^5$, $R^6$, $R^7$ and $R^8$ substituents are hydrogen.

To a mixture of 202 mg (0.5 mmol) of 3,9-diphenylperylene and 3,10-diphenylperylene from example 1.2 and 25 ml of chlorobenzene were added 5 ml of water, 10 ml of chlorobenzene and 800 mg (10 mmol) of bromine, and the mixture was heated at reflux for 22 hours. The reaction mixture was cooled. Thereafter, 200 ml of dilute sodium thiosutfate solution were added at room temperature, the mixture was admixed with ethyl acetate, and the phases were separated and concentrated to obtain the title compounds with an Rf (petroleum ether:toluene 5:1)=0.61.

1.4 Mixture of Compounds of the Formulae (1.a) and (1.b)

280 mg (0.5 mmol) of the mixture obtained in 1.3, 896 mg (10 mmol) of copper cyanide and 30 ml of NMP (N-methylpyrrolidone) were stirred at 100° C. for 6 h and at 150° C. for a further 16 h. After cooling to room temperature, the mixture was precipitated with dilute HCl, and the precipitate was filtered off with suction, washed with water and dried at 60° C. under reduced pressure. The residue was chromatographed on silica gel (eluent:toluene:ethyl acetate 100:1). This gave 17 mg of the title compounds.

Absorption: $\lambda_{max}$ (CH$_2$Cl$_2$): 497 nm;
Emission: $\lambda_{max}$ (CH$_2$Cl$_2$): 563 nm
FQY (polystyrene): 92%
T80 half-life (80 mW/cm$^2$): 59 days in polystyrene Example 2

Mixture of Compounds of the Formulae (2.a) and (2.b)

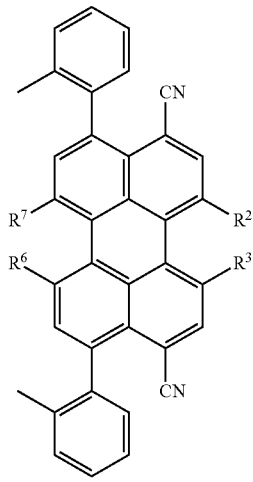

(2.a)

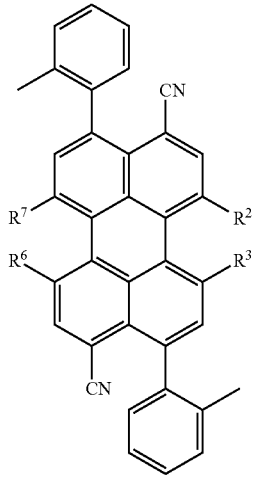

(2.b)

in which
two of the R$^2$, R$^3$, R$^6$ and R$^7$ substituents are hydrogen; and two of the R$^2$, R$^3$, R and R$^7$ substituents are cyano.

2.1 3,9-Bis(o-tolyl)perylene and 3,10-bis(o-tolyl)perylene

A mixture of 4.10 g (10 mmol) of 3,9-dibromoperylene and 3,10-dibromoperylene from example 1.1, 100 ml of toluene, 5.44 g (40 mmol) of 2-methylphenylboronic acid, 8.3 g (60 mmol) of potassium carbonate, 15 ml of water, 2.32 g (2 mmol) of tetrakistriphenylphosphinepalladium was heated to 90° C. for 34 hours. After the reaction mixture had been cooled, it was diluted with toluene, the phases were separated and the toluene phase was purified by means of column filtration with silica gel. This gave 5.54 g of the title compound as a yellow solid, Rf (petroleum ether:toluene 5:1)=0.33, and a by-product with Rf (petroleum ether:toluene 5:1)=0.09.

2.2 Mixture of Compounds of the Formulae (2.2a) and (2.2b)

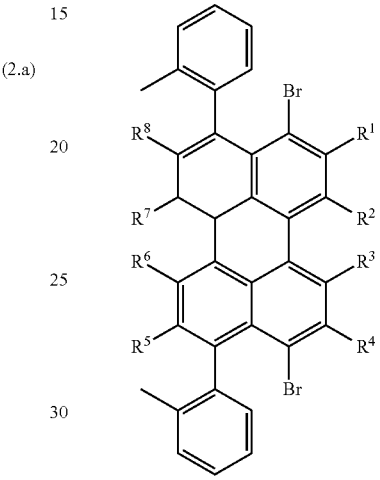

(2.2a)

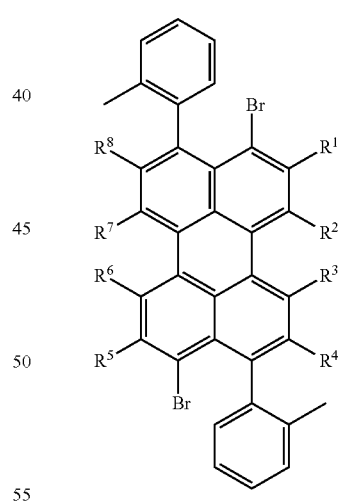

(2.2b)

in which
at least two of the R$^1$, R$^2$, R$^3$, R$^4$, R$^5$, R$^6$, R$^7$ and R$^8$ substituents are bromine, and the other R$^1$, R$^2$, R$^3$, R$^4$, R$^5$, R$^6$, R$^7$ and R$^8$ substituents are hydrogen.

To the mixture of 3,9-bis(o-tolyl)perylene and 3,10-bis(o-tolyl)perylene (1.30 g, 3 mmol) isolated from example 2.1 in 100 ml of chlorobenzene were added, at 40° C., 10 ml of water, 10 ml of chlorobenzene and 4.8 g (60 mmol) of bromine. The mixture was stirred at 70° C. for 16 hours and at 80° C. for 7 hours. The mixture was left to cool to room temperature and diluted with 200 ml of toluene, dilute sodium thiosulfate solution was added, and the phases were separated and concentrated to obtain a residue. The main products formed were tribrominated and tetrabrominated 3,9-bis(o-tolyl)perylene and tribrominated and tetrabrominated 3,10-bis(o-tolyl)perylene, and by-products formed were dibrominated and pentabrominated 3,9-bis(o-tolyl)perylene and 3,10-bis(o-tolyl)perylene. Rf (petroleum ether:toluene 5:1)=0.49, 0.61, 0.38.

2.3 Mixture of Compounds of the Formulae (2.a) and (2.b)

1.12 g of the residue obtained in example 2.2, 2.69 mg (30 mmol) of copper cyanide and 50 ml of N-methylpyrrolidone were stirred at 100° C. for 3 hours and then at 150° C. for 16 hours. The mixture was left to cool to room temperature and dilute HCl was added. The precipitated solid was filtered off with suction, washed with water and dried under reduced pressure at 60° C. The crude title compound was purified on silica gel (eluent:petroleum ether:THF 10:1).

Rf (petroleum ether:THF 5:1)=0.19.
Absorption: $\lambda_{max}$ (CH$_2$Cl$_2$): 489 nm;
Emission: $\lambda_{max}$ (CH$_2$Cl$_2$): 547 nm
FQY (polystyrene): 90-91%;
FQY (polycarbonate): 90-91%;
T80 half-life (80 mW/cm$^2$): 50 days in polystyrene;
T80 half-life (80 mW/cm$^2$): 61 days in polycarbonate.

Example 3

Mixture of Compounds of the Formulae (3.a) and (3.b)

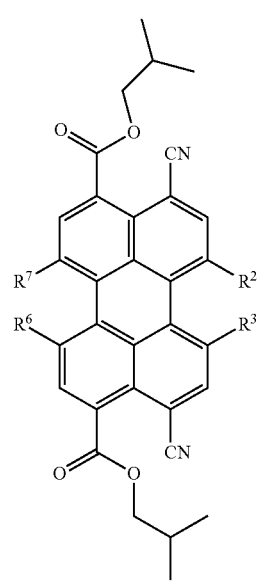
(3.a)

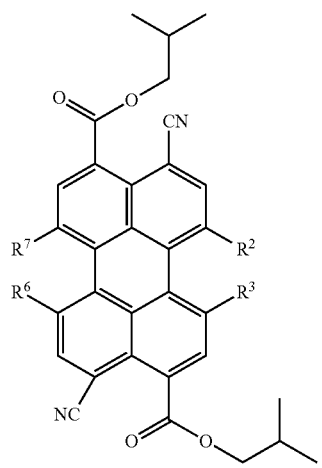
(3.b)

in which
three of the R$^2$, R$^3$, R$^6$ and R$^7$ substituents are hydrogen; and
one of the R$^2$, R$^3$, R$^6$ and R$^7$ substituents is cyano.

3.1 Mixture of Compounds of the Formulae (3.1a) and (3.1b)

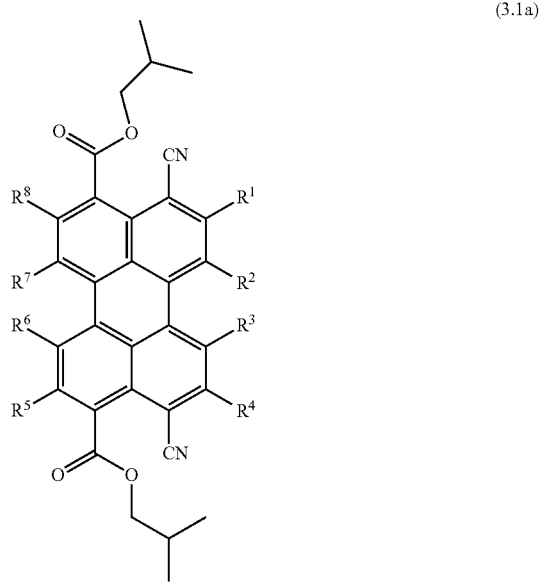
(3.1a)

(3.1b)

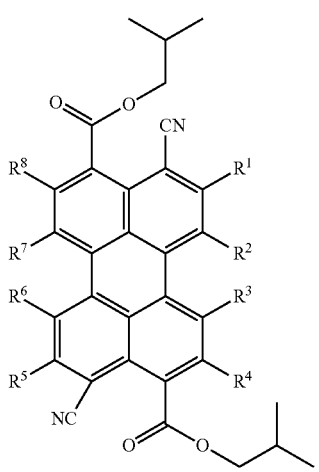

in which
at least one of the $R^1$, $R^2$, $R^3$, $R^4$, $R^5$, $R^6$, $R^7$ and $R^8$ substituents is bromine;
and the other $R^1$, $R^2$, $R^3$, $R^4$, $R^5$, $R^6$, $R^7$ and $R^8$ substituents are hydrogen.

A mixture of 4.52 g (10 mmol) of diisobutyl perylene-3,9-dicarboxylate and diisobutyl perylene-3,10-dicarboxylate, 150 ml of chlorobenzene, 100 ml of water, 16 g (200 mmol) of bromine and a little iodine was stirred under gentle reflux (about 87° C.) for 3 h. Thereafter, the reaction mixture was cooled and poured onto dilute HCl, and the phases were separated. The organic phase was concentrated. The residue had an Rf (toluene:ethyl acetate 10:1)=0.73.

3.2 Preparation of a Mixture of Compounds of the Formulae (3.a) and (3.b)

A mixture of 6 g (7.8 mmol) of the residue obtained in example 3.1, 6.9 g (6.9 mmol) of Cu(I) cyanide and 150 ml of NMP was stirred at 170° C. for 4 h. The reaction mixture was cooled to room temperature, aqueous ammonia was added and extraction was effected with methylene chloride. The residue of the combined organic phases was purified by a column filtration through silica gel (eluent:toluene).
Absorption: $\lambda_{max}$ ($CH_2Cl_2$): 481 nm;
Emission: $\lambda_{max}$ ($CH_2Cl_2$): 511 nm
T80 half-life (80 mW/cm$^2$): 13 days in polystyrene;
T80 half-life (80 mW/cm$^2$): 40 days in polycarbonate.
FQY (polystyrene): 93%;
FQY (polycarbonate): 93%.

The invention claimed is:
1. A cyanated perylene compound of the formula I

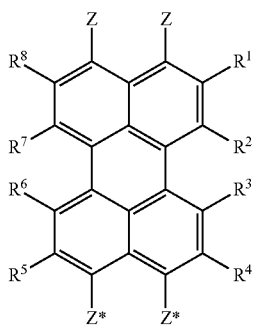

(I)

in which
one of the Z substituents is cyano and the other Z substituent is $CO_2R^9$, $CONR^{10}R^{11}$, $C_1$-$C_{18}$-alkyl, $C_2$-$C_{18}$-alkenyl, $C_2$-$C_{18}$-alkynyl, $C_3$-$C_{12}$-cycloalkyl or $C_6$-$C_{14}$-aryl, where
$C_1$-$C_{18}$-alkyl, $C_2$-$C_{18}$-alkenyl, $C_2$-$C_{18}$-alkynyl are unsubstituted or bear one or more identical or different $Z^a$ substituents,
$C_3$-$C_{12}$-cycloalkyl is unsubstituted or bears one or more identical or different $Z^b$ substituents, and
$C_6$-$C_{14}$-aryl is unsubstituted or bears one or more identical or different $Z^{Ar}$ substituents;
one of the Z* substituents is cyano and the other Z* substituent is $CO_2R^9$, $CONR^{10}R^{11}$, $C_1$-$C_{18}$-alkyl, $C_2$-$C_{18}$-alkenyl, $C_2$-$C_{18}$-alkynyl, $C_3$-$C_{12}$-cycloalkyl or $C_6$-$C_{14}$-aryl, where
$C_1$-$C_{18}$-alkyl, $C_2$-$C_{18}$-alkenyl, $C_2$-$C_{18}$-alkynyl are unsubstituted or bear one or more identical or different $Z^a$ substituents,
$C_3$-$C_{12}$-cycloalkyl is unsubstituted or bears one or more identical or different $Z^b$ substituents, and
$C_6$-$C_{14}$-aryl is unsubstituted or bears one or more identical or different $Z^{Ar}$ substituents;
$R^1$, $R^2$, $R^3$, $R^4$, $R^5$, $R^6$, $R^7$ and $R^8$ are each independently selected from hydrogen, cyano, bromine and chlorine, with the proviso that 1, 2, 3, 4, 5, 6, 7 or 8 of the $R^1$, $R^2$, $R^3$, $R^4$, $R^5$, $R^6$, $R^7$ or $R^8$ substituents are cyano;
where
$R^9$ is hydrogen, $C_1$-$C_{10}$-alkyl, $C_2$-$C_{10}$-alkenyl, $C_2$-$C_{10}$-alkynyl, $C_3$-$C_{12}$-cycloalkyl or $C_6$-$C_{14}$-aryl, where
$C_1$-$C_{10}$-alkyl, $C_2$-$C_{10}$-alkenyl, $C_2$-$C_{10}$-alkynyl are unsubstituted or bear one or more identical or different $R^a$ substituents,
$C_3$-$C_{12}$-cycloalkyl is unsubstituted or bears one or more identical or different $R^b$ substituents and
$C_6$-$C_{14}$-aryl is unsubstituted or bears one or more identical or different $R^{Ar}$ substituents;
$R^{10}$ and $R^{11}$ are each independently hydrogen, $C_1$-$C_{10}$-alkyl, $C_2$-$C_{10}$-alkenyl, $C_2$-$C_{10}$-alkynyl, $C_3$-$C_{12}$-cycloalkyl or $C_6$-$C_{14}$-aryl, where
$C_1$-$C_{10}$-alkyl, $C_2$-$C_{10}$-alkenyl, $C_2$-$C_{10}$-alkynyl are unsubstituted or bear one or more identical or different $R^a$ substituents,
$C_3$-$C_{12}$-cycloalkyl is unsubstituted or bears one or more identical or different $R^b$ substituents and
$C_6$-$C_{14}$-aryl is unsubstituted or bears one or more identical or different $R^{Ar}$ substituents;
each $Z^a$ is independently halogen, hydroxyl, $NR^{10a}R^{11a}$, $C_1$-$C_{10}$-alkoxy, $C_1$-$C_{10}$-haloalkoxy, $C_1$-$C_{10}$-alkylthio, $C_3$-$C_{12}$-cycloalkyl, $C_6$-$C_{14}$-aryl, $C(=O)R^{9a}$, $C(=O)OR^{9a}$ or $C(O)NR^{10a}R^{11a}$, where
$C_3$-$C_{12}$-cycloalkyl is unsubstituted or bears one or more identical or different $R^b$ substituents and
$C_6$-$C_{14}$-aryl is unsubstituted or bears one or more identical or different $R^{Ar}$ substituents;
each $Z^b$ and each $Z^{Ar}$ is independently halogen, hydroxyl, $NR^{10a}R^{11a}$, $C_1$-$C_{10}$-alkyl, $C_1$-$C_{10}$-alkoxy, $C_1$-$C_{10}$-haloalkoxy, $C_1$-$C_{10}$-alkylthio, $C(=O)R^{9a}$, $C(=O)OR^{9a}$ or $C(O)NR^{10a}R^{11a}$;
each $R^a$ is independently halogen, hydroxyl, $C_1$-$C_{10}$-alkoxy, $C_3$-$C_{12}$-cycloalkyl or $C_6$-$C_{14}$-aryl;
each $R^b$ is independently halogen, hydroxyl, $C_1$-$C_{10}$-alkyl, $C_1$-$C_{10}$-alkoxy, $C_1$-$C_{10}$-haloalkoxy, $C_1$-$C_{10}$-alkylthio, $C_2$-$C_{10}$-alkenyl, $C_2$-$C_{10}$-alkynyl, $C_3$-$C_{12}$-cycloalkyl or $C_6$-$C_{14}$-aryl;
each $R^{Ar}$ is independently halogen, hydroxyl, $C_1$-$C_{10}$-alkyl, $C_1$-$C_{10}$-alkoxy, $C_1$-$C_{10}$-haloalkoxy, $C_1$-$C_{10}$- alkylthio, $C_2$-$C_{10}$-alkenyl, $C_2$-$C_{10}$-alkynyl, $C_3$-$C_{12}$-cycloalkyl or $C_6$-$C_{14}$-aryl;

$R^{9a}$ is hydrogen, $C_1$-$C_{10}$-alkyl, $C_2$-$C_{10}$-alkenyl, $C_2$-$C_{10}$-alkynyl, $C_3$-$C_{12}$-cycloalkyl or $C_6$-$C_{14}$-aryl; and $R^{10a}$, $R^{11a}$ are each independently hydrogen, $C_1$-$C_{10}$-alkyl, $C_2$-$C_{10}$-alkenyl, $C_2$-$C_{10}$-alkynyl, $C_3$-$C_{12}$-cycloalkyl or $C_6$-$C_{14}$-aryl, and mixtures thereof.

2. A cyanated perylene compound of the formula I according to claim 1, in which 1, 2, 3 or 4 of the $R^1$, $R^2$, $R^3$, $R^4$, $R^5$, $R^6$, $R^7$ or $R^8$ substituents are cyano.

3. A cyanated perylene compound of the formula I according to claim 1, in which none of the $R^1$, $R^2$, $R^3$, $R^4$, $R^5$, $R^6$, $R^7$ or $R^8$ substituents are bromine or chlorine.

4. A cyanated perylene compound of the formula I according to claim 1, in which one or two of the $R^1$, $R^2$, $R^3$, $R^4$, $R^5$, $R^6$, $R^7$ or $R^8$ substituents are cyano and the other $R^1$, $R^2$, $R^3$, $R^4$, $R^5$, $R^6$, $R^7$ or $R^8$ substituents are hydrogen.

5. A cyanated perylene compound of the formula I according to claim 1, in which one of the Z substituents and one of the Z* substituents are independently selected from $C_1$-$C_{10}$-alkyl, $CO_2R^9$, phenyl-$C_1$-$C_{10}$-alkyl and phenyl, where phenyl and the phenyl moiety of phenyl-$C_1$-$C_{10}$-alkyl are unsubstituted or bear one or more substituents selected from $C_1$-$C_6$-alkyl, and where $R^9$ is as defined above.

6. A cyanated perylene compound of the formula I according to claim 1, selected from compounds of the formulae (1), (2), (3), (4), (5), (6), (7), (8), (9), (10), (11), (12), (13), (14), (15), (16), (17), (18), (19), and (20)

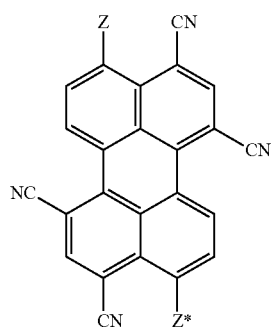

(1)

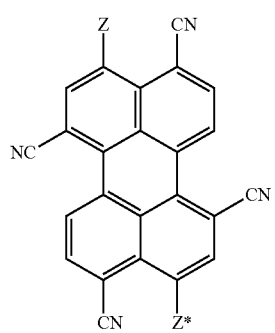

(2)

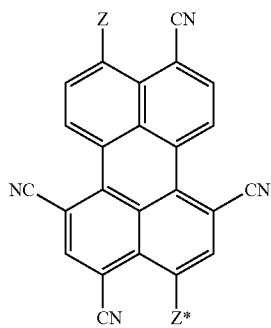

(3)

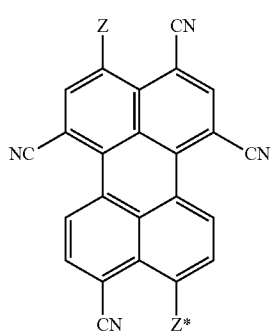

(4)

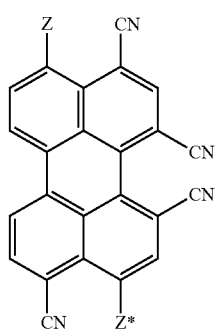

(5)

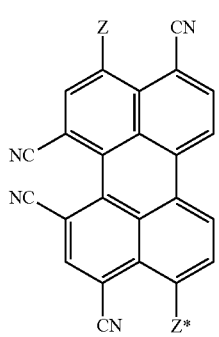

(6)

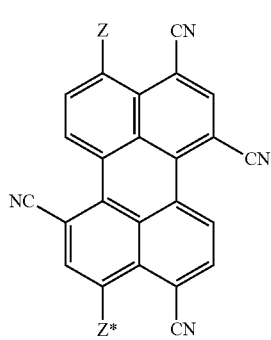

(7)

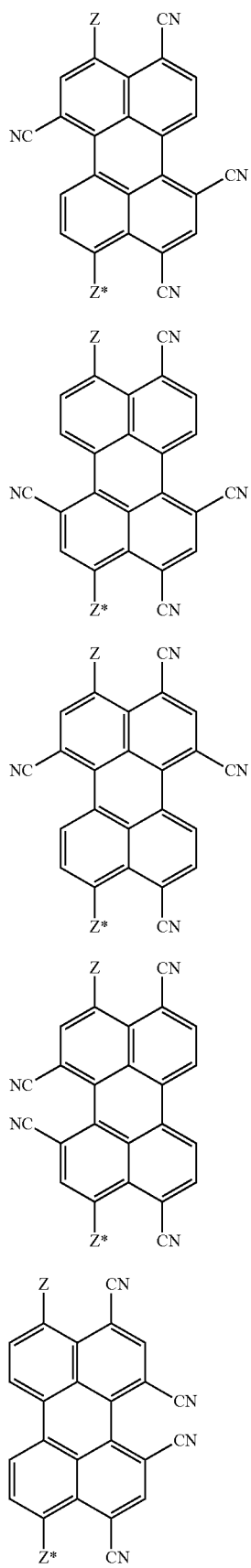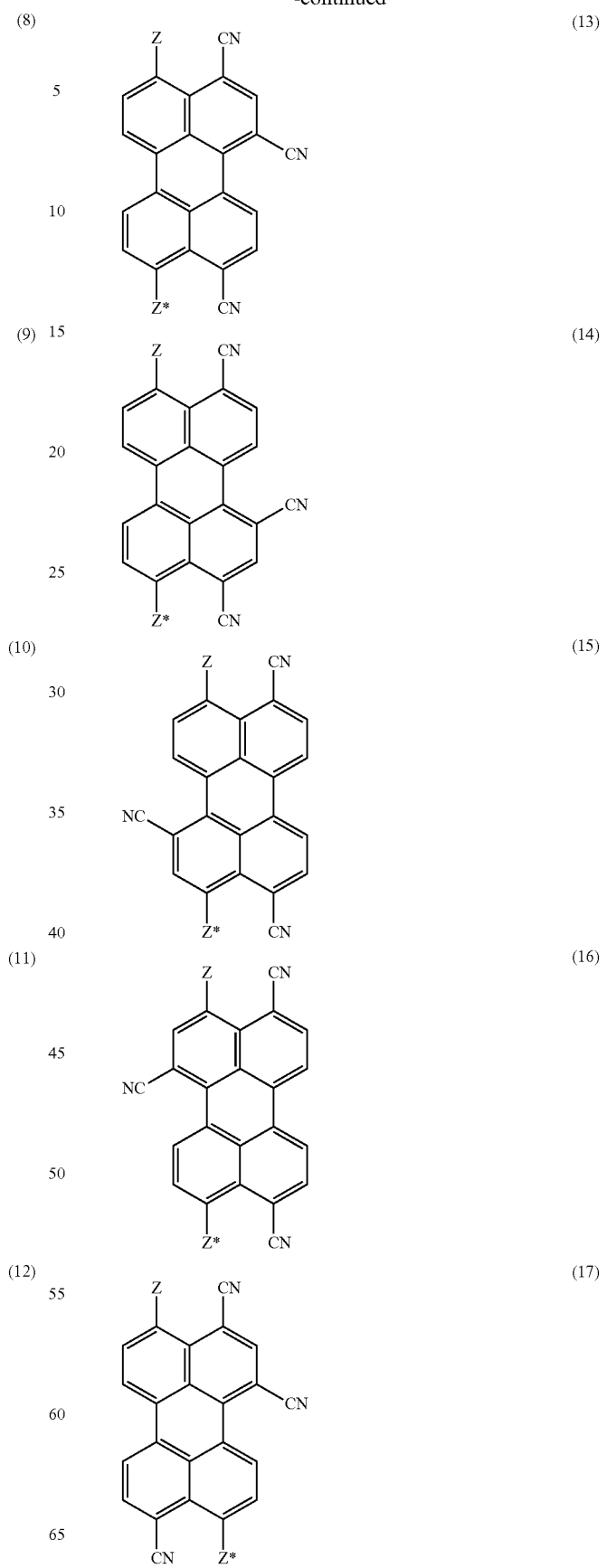

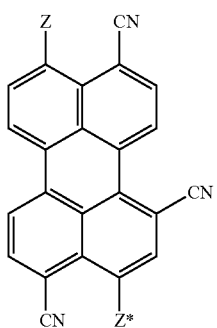

(18)

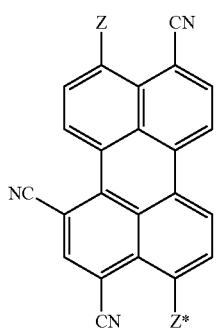

(19)

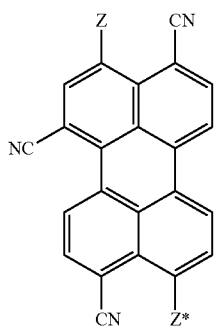

(20)

in which

Z is selected from $C_1$-$C_6$-alkyl, $C_1$-$C_6$-alkoxycarbonyl, phenyl, and phenyl bearing 1, 2 or 3 $C_1$-$C_4$-alkyl groups; and Z* is selected from $C_1$-$C_6$-alkyl, $C_1$-$C_6$-alkoxycarbonyl, phenyl, and phenyl bearing 1, 2 or 3 $C_1$-$C_4$-alkyl groups;

and mixtures thereof.

7. A composition comprising at least one cyanated perylene compound of the formula I according to claim 1.

8. The composition according to claim 7, comprising at least one cyanated perylene compound of the formula I-A

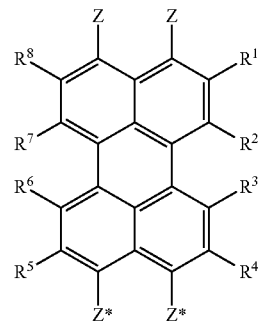

(I-A)

in which one of the Z substituents is cyano and the other Z substituent is $C_1$-$C_{18}$-alkyl, $C_2$-$C_{18}$-alkenyl, $C_2$-$C_{18}$-alkynyl, $C_3$-$C_{12}$-cycloalkyl or $C_6$-$C_{14}$-aryl, where
  $C_1$-$C_{18}$-alkyl, $C_2$-$C_{18}$-alkenyl, $C_2$-$C_{18}$-alkynyl are unsubstituted or bear one or more identical or different $Z^a$ substituents, where $Z^a$ is as defined above,
  $C_3$-$C_{12}$-cycloalkyl is unsubstituted or bears one or more identical or different $Z^b$ substituents, where $Z^b$ is as defined above; and
  $C_6$-$C_{14}$-aryl is unsubstituted or bears one or more identical or different $Z^{Ar}$ substituents, where $Z^{Ar}$ is as defined above;

one of the Z* substituents is cyano and the other Z* substituent is $C_1$-$C_{18}$-alkyl, $C_2$-$C_{18}$-alkenyl, $C_2$-$C_{18}$-alkynyl, $C_3$-$C_{12}$-cycloalkyl or $C_6$-$C_{14}$-aryl, where
  $C_1$-$C_{18}$-alkyl, $C_2$-$C_{18}$-alkenyl, $C_2$-$C_{18}$-alkynyl are unsubstituted or bear one or more identical or different $Z^a$ substituents, where $Z^a$ is as defined above,
  $C_3$-$C_{12}$-cycloalkyl is unsubstituted or bears one or more identical or different $Z^b$ substituents, where $Z^b$ is as defined above; and
  $C_6$-$C_{14}$-aryl is unsubstituted or bears one or more identical or different $Z^{Ar}$ substituents, where $Z^{Ar}$ is as defined above;

$R^1$, $R^4$, $R^5$ and $R^8$ are each hydrogen;

two of the $R^2$, $R^3$, $R^6$ or $R^7$ substituents are hydrogen; and the other $R^2$, $R^3$, $R^6$ or $R^7$ substituents are cyano;

or mixtures thereof, obtainable by a process, comprising:

a) halogenating a perylene of the formula II

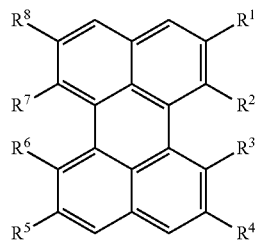

(II)

in which $R^1$, $R^2$, $R^3$, $R^4$, $R^5$, $R^6$, $R^7$ and $R^8$ are each hydrogen;

to obtain a mixture of 3,9-dihaloperylene of the formula IIIa and 3,10-dihaloperylene of the formula IIIb

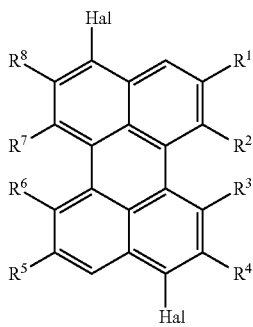

(IIIa)

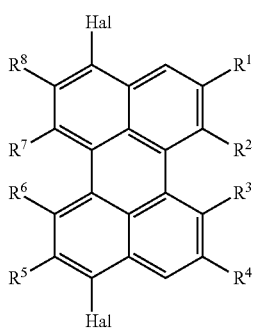

(IIIb)

in which
R$^1$, R$^2$, R$^3$, R$^4$, R$^5$, R$^6$, R$^7$ and R$^8$ are each hydrogen; and
Hal are each all chlorine or bromine;

b) reacting the mixture of compounds of the formulae IIIa and IIIb obtained in
a) with an organometallic compound of the formula IV Z-Met (IV)

and optionally with an organometallic compound of the formula V

Z*-Met (V)

in which
Z is selected from C$_1$-C$_{18}$-alkyl, C$_2$-C$_{18}$-alkenyl, C$_2$-C$_{18}$-alkynyl, C$_3$-C$_{12}$-cycloalkyl and C$_6$-C$_{14}$-aryl, where C$_1$-C$_{18}$-alkyl, C$_2$-C$_{18}$-alkenyl, C$_2$-C$_{18}$-alkynyl are unsubstituted or bear one or more identical or different Z$^a$ substituents,
  C$_3$-C$_{12}$-cycloalkyl is unsubstituted or bears one or more identical or different Z$^b$ substituents, and
  C$_6$-C$_{14}$-aryl is unsubstituted or bears one or more identical or different Z$^{Ar}$ substituents;
Z* is selected from C$_1$-C$_{18}$-alkyl, C$_2$-C$_{18}$-alkenyl, C$_2$-C$_{18}$-alkynyl, C$_3$-C$_{12}$-cycloalkyl and C$_6$-C$_{14}$-aryl, where C$_1$-C$_{18}$-alkyl, C$_2$-C$_{18}$-alkenyl, C$_2$-C$_{18}$-alkynyl are unsubstituted or bear one or more identical or different Z$^a$ substituents,
  C$_3$-C$_{12}$-cycloalkyl is unsubstituted or bears one or more identical or different Z$^b$ substituents, and
  C$_6$-C$_{14}$-aryl is unsubstituted or bears one or more identical or different Z$^{Ar}$ substituents;
  where Z* may also be as defined for Z;
Met is B(OH)$_2$, B(OR')(OR''), Zn-Hal or Sn(R*)$_3$, in which
R' and R'' are each independently hydrogen, C$_1$-C$_{30}$-alkyl, C$_5$-C$_8$-cycloalkyl, C$_6$-C$_{14}$-aryl or heteroaryl or
  R and R'' together are C$_2$-C$_4$-alkylene which optionally bears 1, 2, 3, 4, 5, 6, 7 or 8 substituents selected from C$_1$-C$_4$-alkyl, C$_5$-C$_8$-cycloalkyl, C$_6$-C$_{14}$-aryl and heteroaryl;
Hal is chlorine or bromine; and
R* is C$_1$-C$_8$-alkyl or phenyl;
to obtain a mixture of compounds of the formulae VIa and VIb

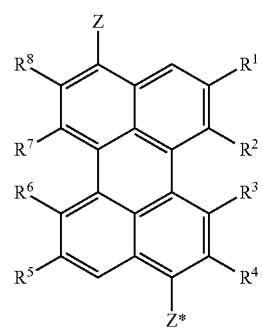

(VIa)

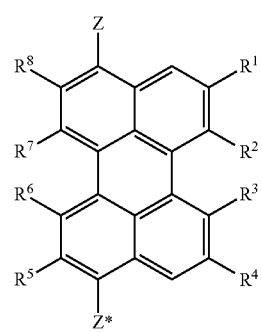

(VIb)

in which
R$^1$, R$^2$, R$^3$, R$^4$, R$^5$, R$^6$, R$^7$ and R$^8$ are each hydrogen; and
Z and Z* are each as defined above;

c) halogenating the mixture of compounds of the formulae VIa and VIb obtained in b) to obtain a reaction mixture comprising compounds of the formulae VIIa and VIIb

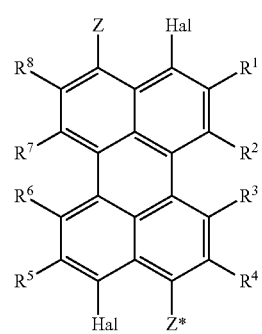

(VIIa)

-continued

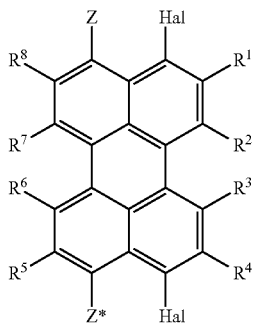

(VIIb)

in which
Z and Z* are each as defined above,
Hal is halogen selected from chlorine and bromine, where the Hal substituents are either all chlorine or all bromine;
$R^1$, $R^2$, $R^3$, $R^4$, $R^5$, $R^6$, $R^7$ and $R^8$ are each hydrogen or halogen selected from chlorine and bromine, where the $R^1$, $R^2$, $R^3$, $R^4$, $R^5$, $R^6$, $R^7$ and $R^8$ substituents that are not hydrogen are either all chlorine or all bromine;

d) substituting halogen atoms of the compounds of the formulae VIIa and VIIb present in the reaction mixture obtained in c) for cyano groups, and optionally partly for hydrogen, to obtain at least one compound of the formula I-A or mixtures thereof; and, optionally, e) separating and/or purifying the at least one compound of the formula I-A or mixtures thereof present in the reaction mixture obtained in d).

9. The composition according to claim 8, in which, in formula I-A,
one of the Z substituents is cyano and the other Z substituent is $C_1$-$C_6$-alkyl, phenyl, or phenyl bearing 1, 2 or 3 $C_1$-$C_4$-alkyl groups;
one of the Z* substituents is cyano and the other Z* substituent is $C_1$-$C_6$-alkyl, phenyl, or phenyl bearing 1, 2 or 3 $C_1$-$C_4$-alkyl groups;
$R^1$, $R^4$, $R^5$ and $R^8$ are each hydrogen;
two of the $R^2$, $R^3$, $R^6$ or $R^7$ substituents are cyano and the other $R^2$, $R^3$, $R^6$ or $R^7$ substituents are hydrogen.

10. The composition according to claim 7, comprising at least one cyanated perylene compound of the formula I-B

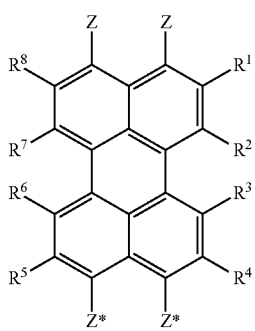

(I-B)

in which
one of the Z substituents is cyano and the other Z substituent is $COOR^9$;
one of the Z* substituents is cyano and the other Z* substituent is $COOR^9$;
$R^1$, $R^4$, $R^5$ and $R^8$ are each hydrogen;

one of the $R^2$, $R^3$, $R^6$ or $R^7$ substituents is cyano and the other $R^2$, $R^3$, $R^6$ or $R^7$ substituents are hydrogen; and
$R^9$ is hydrogen, $C_1$-$C_{10}$-alkyl, $C_2$-$C_{10}$-alkenyl, $C_2$-$C_{10}$-alkynyl, $C_3$-$C_{12}$-cycloalkyl or $C_6$-$C_{14}$-aryl, where
$C_1$-$C_{10}$-alkyl, $C_2$-$C_{10}$-alkenyl, $C_2$-$C_{10}$-alkynyl are unsubstituted or bear one or more identical or different $R^a$ substituents,
$C_3$-$C_{12}$-cycloalkyl is unsubstituted or bears one or more identical or different $R^b$ substituents and
$C_6$-$C_{14}$-aryl is unsubstituted or bears one or more identical or different $R^{Ar}$ substituents,
where $R^a$, $R^b$ and $R^{Ar}$ are each as defined above;
or mixtures thereof,
obtainable by a process comprising:
f) a mixture of perylene compounds of the formulae VIIIa and VIIIb

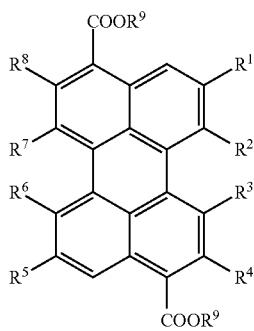

(VIIIa)

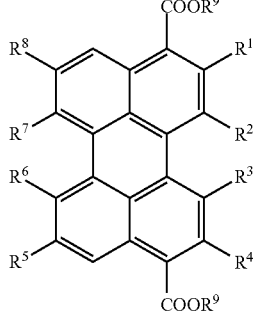

(VIIIb)

in which
$R^1$, $R^2$, $R^3$, $R^4$, $R^5$, $R^6$, $R^7$ and $R^8$ are hydrogen; and
$R^9$ is as defined above
to obtain a reaction mixture comprising compounds of the formulae IXa and IXb

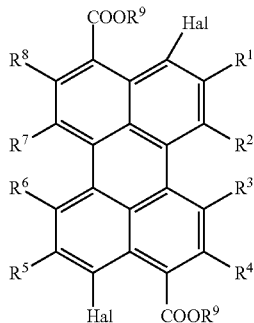

(IXa)

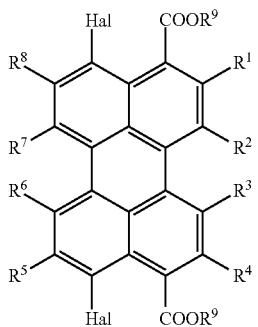

(IXb)

in which

R$^1$, R$^2$, R$^3$, R$^4$, R$^5$, R$^6$, R$^7$ and R$^8$ are each hydrogen or halogen selected from chlorine and bromine, where the R$^1$, R$^2$, R$^3$, R$^4$, R$^5$, R$^6$, R$^7$ and R$^8$ substituents that are not hydrogen are either all chlorine or all bromine;

Hal is halogen selected from chlorine and bromine, where the Hal substituents are either all chlorine or all bromine; and R$^9$ is as defined above;

g) substituting halogen atoms of the compounds of the formulae IXa and IXb present in the reaction mixture obtained in f) for cyano groups, and optionally partly for hydrogen, to obtain at least one compound of the formula I-B or mixtures thereof; and h) separating and/or purifying the at least one compound of the formula I-B or mixtures thereof present in the reaction mixture obtained in g).

11. The composition according to claim 10, in which, in formula I-B, one of the Z substituents is cyano and the other Z substituent is C$_1$-C$_6$-alkoxycarbonyl;

one of the Z* substituents is cyano and the other Z* substituent is C$_1$-C$_6$-alkoxycarbonyl;

R$^1$, R$^4$, R$^5$ and R$^8$ are each hydrogen;

one of the R$^2$, R$^3$, R$^6$ or R$^7$ substituents is cyano and the other R$^2$, R$^3$, R$^6$ or R$^7$ substituents are each hydrogen.

* * * * *